US012277999B2

(12) United States Patent
Milenkovic et al.

(10) Patent No.: US 12,277,999 B2
(45) Date of Patent: *Apr. 15, 2025

(54) RE-WRITABLE DNA-BASED DIGITAL STORAGE WITH RANDOM ACCESS

(71) Applicant: The Board of Trustees of the University of Illinois, Urbana, IL (US)

(72) Inventors: Olgica Milenkovic, Urbana, IL (US); S. M. Hossein Tabatabaei Yazdi, Urbana, IL (US); Yongbo Yuan, Urbana, IL (US); Jian Ma, Urbana, IL (US); Huimin Zhao, Champaign, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 1250 days.

This patent is subject to a terminal disclaimer.

(21) Appl. No.: 16/653,564

(22) Filed: Oct. 15, 2019

(65) Prior Publication Data
US 2020/0035331 A1 Jan. 30, 2020

Related U.S. Application Data

(63) Continuation of application No. 15/356,118, filed on Nov. 18, 2016, now Pat. No. 10,566,077.
(Continued)

(51) Int. Cl.
*G16B 50/00* (2019.01)
*B01J 19/00* (2006.01)
*G16B 25/20* (2019.01)

(52) U.S. Cl.
CPC .......... *G16B 50/00* (2019.02); *B01J 19/0046* (2013.01); *G16B 25/20* (2019.02);
(Continued)

(58) Field of Classification Search
CPC .............. G16B 50/00; G16B 25/20; B01J 2219/00722; B01J 19/0046; B01J 2219/0059; B01J 2219/00596
See application file for complete search history.

(56) References Cited

U.S. PATENT DOCUMENTS 6,223,128 B1  4/2001  Allex et al.
7,227,900 B2  6/2007  Porter
(Continued)

FOREIGN PATENT DOCUMENTS

WO    2008087042 A1    7/2008

OTHER PUBLICATIONS

Rosseel, T., Lambrecht, B., Vandenbussche, F. et al. Identification and complete genome sequencing of paramyxoviruses in mallard ducks (*Anas platyrhynchos*) using random access amplification and next generation sequencing technologies. Virol J 8, 463 (2011). https://doi.org/10.1186/1743-422X-8-463 (Year: 2011).*
(Continued)

*Primary Examiner* — Karlheinz R. Skowronek
*Assistant Examiner* — Emilie A Neulen
(74) *Attorney, Agent, or Firm* — McDonnell Boehnen Hulbert & Berghoff LLP

(57) ABSTRACT

The disclosure relates to a re-writable DNA-based digital storage system with a random access feature. An example embodiment includes reading a physical nucleotide sequence of 2n+L bases to form a digital representation of the physical nucleotide sequence; dividing the digital representation of the physical nucleotide sequence into an address representation of n bases, followed by a data representation of L bases, followed by a further address representation of n bases; decoding the data representation into an integer value less than 3L that is a sum of a first addend and a second addend, wherein the data representation includes a
(Continued)

first subsequence of bases encoding the first addend followed by a second subsequence of bases encoding the second addend; and storing, in a computer memory, the integer value.

20 Claims, 12 Drawing Sheets

Specification includes a Sequence Listing.

Related U.S. Application Data

(60) Provisional application No. 62/257,273, filed on Nov. 19, 2015.

(52) U.S. Cl.
CPC ............... *B01J 2219/0059* (2013.01); *B01J 2219/00596* (2013.01); *B01J 2219/00722* (2013.01)

(56) References Cited

U.S. PATENT DOCUMENTS

| | | | |
|---|---|---|---|
| 9,996,778 | B2 | 6/2018 | Church |
| 10,370,246 | B1 | 8/2019 | Milenkovic |
| 11,538,554 | B1 | 12/2022 | Milenkovic |
| 2004/0001371 | A1 | 1/2004 | Mansuripur et al. |
| 2005/0053968 | A1 | 3/2005 | Bharadwaj et al. |
| 2015/0261664 | A1 | 9/2015 | Goldman et al. |
| 2017/0141793 | A1 | 5/2017 | Strauss et al. |
| 2018/0127804 | A1 | 5/2018 | Dean et al. |
| 2020/0004926 | A1 | 1/2020 | Strauss |
| 2020/0185057 | A1 | 6/2020 | Leake |
| 2021/0074380 | A1 | 3/2021 | Yekhanin |
| 2021/0098081 | A1 | 4/2021 | Yekhanin |
| 2021/0103824 | A1 | 4/2021 | Milenkovic |
| 2021/0125079 | A1 | 4/2021 | Milenkovic |
| 2021/0191970 | A1 | 6/2021 | Pan |

OTHER PUBLICATIONS

D. Limbachiya, V. Dhameliya, M. Khakhar and M. K. Gupta, "On optimal family of codes for archival DNA storage," 2015 Seventh International Workshop on Signal Design and its Applications in Communications (IWSDA), Bengaluru, India, 2015, pp. 123-127, doi: 10.1109/IWSDA.2015.7458386. (Year: 2015).*
Guerrero Fernández, Darío & Larrosa, Rafael & Gonzalo, Claros. (2013). FQbin: a compatible and optimized format for storing and managing sequence data. Current Bioinformatics. (Year: 2013).*
Tabatabaei Yazdi, S. M. H., et al.; "A Rewritable, Random-Access DNA-Based Storage System."; Sci. Rep. 5, 14138; doi: 10.1038/srep14138 (Sep. 18, 2015).
Tabatabaei Yazdi, S. M. H., et al.; Supplementary Information for "A Rewritable, Random-Access DNA-Based Storage System"; Sci. Rep. 5, 14138 (Sep. 18, 2015).
Tabatabaei Yazdi, S. M. H., et al.; "Weakly Mutually Uncorrelated Codes"; arXiv: 1601.08176; Published to arxiv.org on Jan. 29, 2016.
Bancroft, C., et al.; "Long-term storage of information in DNA."; Science 293, 1763-1765 (2001).
Davis, J.; "Microvenus"; Art Journal 55, 70-74 (1996).
Church, G. M., et al.; "Next-generation digital information storage in DNA."; Science 337, 1628-1628 (2012).
Goldman, N., et al.; "Towards practical, high-capacity, low-maintenance information storage in synthesized DNA."; Nature 494, 77-80 (2013).
Grass, R. N., et al.; "Robust chemical preservation of digital information on DNA in silica with error-correcting codes."; Angewandte Chemie International Edition 54, 2552-2555 (Feb. 4, 2015).
Ross, M. G., et al.; "Characterizing and measuring bias in sequence data."; Genome Biol 14, R51 (2013).
Cohen, G. D., et al.; "Dc-constrained error-correcting codes with small running digital sum."; Information Theory, IEEE Transactions on 37, 949-955 (1991).
Blaum, M., et al.; "Error-correcting codes with bounded running digital sum."; IEEE transactions on information theory 39, 216-227 (1993).
Gilbert, E.; "Synchronization of binary messages."; Information Theory, IRE Transactions on 6, 470-477 (1960).
Packer, H.; "CRISPR and Cas9 for flexible genome editing."; Technical report. (2014); Available at: www.idtdna.com/pages/products/genes/gblocks-gene-fragments/decoded-articles/decoded/2013/12/13/crispr-and-cas9-for-flexible-genome-editing. (Accessed: Jan. 1, 2015).
Bryksin, A. V., et al.; "Overlap extension PCR cloning: a simple and reliable way to create recombinant plasmids."; Biotechniques 48, 463 (2010).
Schuster, S. C.; "Next-generation sequencing transforms today's biology."; Nature methods 5, 16-18 (2008).
Morita, H., et al.; "On the construction of maximal prefix-synchronized codes."; Information Theory, IEEE Transactions on 42, 2158-2166 (1996).
Milenkovic, O., et al.; "On the design of codes for DNA computing."; In Coding and Cryptography, 100-119 (Springer, 2006).
Rouillard, J.-M., et al.; "Oligoarray 2.0: design of oligonucleotide probes for DNA microarrays using a thermodynamic approach."; Nucleic acids research 31, 3057-3062 (2003).
Guibas, L. J., et al.; "Maximal prefix-synchronized codes."; SIAM Journal on Applied Mathematics 35, 401-418 (1978).
Massey, J. L.; "Optimum frame synchronization."; Communications, IEEE Transactions on 20, 115-119 (1972).
Chee, Y. M., et al.; "Cross-bifix-free codes within a constant factor of optimality."; Information Theory, IEEE Transactions on 59, 4668-4674 (2013).
Blackburn, S. R.; "Non-overlapping codes."; arXiv preprint arXiv:1303.1026 (2013).
Berman, P., et al.; "Approximating maximum independent set in bounded degree graphs."; In SODA, vol. 94, 365-371 (1994).
R. G. Gallager; "Low-density parity-check codes, Information Theory"; IRE Transactions on, vol. 8, No. 1, pp. 2128, (1962).
A. J. De Lind Van Wijngaarden, et al.; "Frame synchronization using distributed sequences,"; Communications, IEEE Transactions on, vol. 48, No. 12, pp. 2127-2138 (2000).
D. Baji'c, et al.; "Distributed sequences and search process,"; Communications, IEEE International Conference on, vol. 1. IEEE, 2004, pp. 514-518 (2004).
S. Bilotta, et al.; "A new approach to cross-bifix-free sets,"; IEEE Transactions on Information Theory, vol. 6, No. 58, pp. 4058-4063 (2012).
H. M. Kiah, et al.; "Codes for dna sequence profiles,"; arXiv preprint; arXiv:1502.00517, published to arxiv.org on Feb. 2, 2015.
Tabatabaei Yazdi, S. M. H., et al.; "DNA-Based Storage: Trends and Methods"; arXiv:1507.01611; published to arxiv.org on Jul. 6, 2015.
D. E. Knuth; "Efficient balanced codes,"; Information Theory, IEEE Transactions on, vol. 32, No. 1, pp. 51-53 (1986).
E. N. Gilbert; "A comparison of signalling alphabets,"; Bell System Technical Journal, vol. 31, No. 3, pp. 504-522 (1952).
R. L. Graham, et al.; "Lower bounds for constant weight codes,"; Information Theory, IEEE Transactions on, vol. 26, No. 1, pp. 37-43 (1980).
S. M. Johnson; "A new upper bound for error-correcting codes,"; Information Theory, IRE Transactions on, vol. 8, No. 3, pp. 203-207 (1962).
S. Tavares; "A study of synchronization techniques for binary cyclic codes,"; Ph.D. dissertation, Thesis (Ph. D.)—McGill University (1968).
"GBlocks (TM) Gene Fragments Cloning Protocols"; http://www.idtdna.com/pages/docs/synthetic-biology/gblocks-user-guide.pdf; retrieved Nov. 15, 2016.
"Overlap Extension Polymerase Chain Reaction"—Wikipedia article; https://en.wikipedia.org/wiki/Overlap_extension_polymerase_chain_reaction; retrieved Nov. 15, 2016.

(56) References Cited

OTHER PUBLICATIONS

I. S. Reed, et al.; "Polynomial codes over certain finite fields,"; Journal of the society for industrial and applied mathematics, vol. 8, No. 2, pp. 300-304 (1960).

H. M. Kiah, et al.; "Codes for dna storage channels,"; arXiv preprint arXiv:1410.8837, published to arxiv.org on Oct. 31, 2014.

R. Gabrys, et al.; "Asymmetric lee distance codes for dna-based storage,"; arXiv preprint arXiv:1506.00740, published to arxiv.org on Jun. 2, 2015.

S. Kosuri, et al.; "Large-scale de novo dna synthesis: technologies and applications,"; Nature methods, vol. 11, No. 5, pp. 499-507 (2014).

J. Tian, et al.; "Advancing high-throughput gene synthesis technology,"; Molecular BioSystems, vol. 5, No. 7, pp. 714-722 (2009).

S. Ma, et al.; "Dna synthesis, assembly and applications in synthetic biology,"; Current opinion in chemical biology, vol. 16, No. 3, pp. 260-267 (2012).

S. Ma, et al.; "Error correction in gene synthesis technology,"; Trends in biotechnology, vol. 30, No. 3, pp. 147-154 (2012).

A. Michelson, et al.; "Nucleotides part xxxii. synthesis of a dithymidine dinucleotide containing a 3': 5'-internucleotidic linkage,"; Journal of the Chemical Society (Resumed), pp. 2632-2638 (1955).

R. Hall, et al.; "644. nucleotides. part xli. mixed anhydrides as intermediates in the synthesis of dinucleoside phosphates,"; Journal of the Chemical Society (Resumed), pp. 3291-3296 (1957).

D. R. Zerbino, et al.; "Velvet: algorithms for de novo short read assembly using de Bruijn graphs,"; Genome Res., vol. 18, No. 5, pp. 821-829 (May 2008).

S. Gnerre, et al.; "High-quality draft assemblies of mammalian genomes from massively parallel sequence data,"; Proc. Natl. Acad. Sci. U.S.A., vol. 108, No. 4, pp. 1513-1518 (Jan. 2011).

R. Li, et al.; "De novo assembly of human genomes with massively parallel short read sequencing," Genome Res., vol. 20, No. 2, pp. 265-272 (Feb. 2010).

J. T. Simpson, et al.; "ABySS: a parallel assembler for short read sequence data,"; Genome Res., vol. 19, No. 6, pp. 1117-1123 (Jun. 2009).

J. T. Simpson, et al.; "Efficient de novo assembly of large genomes using compressed data structures,"; Genome Res., vol. 22, No. 3, pp. 549-556 (Mar. 2012).

S. Kannan, et al.; "More on reconstructing strings from random traces: insertions and deletions,"; Proc. IEEE Intl. Inform. Theory; IEEE; pp. 297-301. (2005).

J. Acharya, et al.; "On reconstructing a string from its substring compositions,"; Proc. IEEE Intl. Symp. Inform. Theory; IEEE; pp. 1238-1242 (2010).

J. Acharya, et al.; "Quadratic-backtracking algorithm for string reconstruction from substring compositions,"; Proc. IEEE Intl. Symp. Inform. Theory; IEEE; pp. 1296-1300 (2014).

P. Medvedev, et al.; "Computability of models for sequence assembly,"; Algorithms in Bioinformatics; Springer; pp. 289-301 (2007).

P. E. Compeau, et al.; "How to apply de Bruijn graphs to genome assembly,"; Nature biotechnology, vol. 29, No. 11, pp. 987-991 (2011).

P. Jacquet, et al.; "Counting Markov types, balanced matrices, and Eulerian graphs,"; IEEE Trans. Inform. Theory; vol. 58, No. 7, pp. 4261-4272 (2012).

K. Nakamura, et al.; "Sequence-specific error profile of Illumina sequencers,"; Nucleic acids research; p. gkr344, (2011).

T. Kløve; "Error correcting codes for the asymmetric channel."; Department of Pure Mathematics, University of Bergen, (1981).

E. Ukkonen; "Approximate string-matching with q-grams and maximal matches,"; Theoretical computer science, vol. 92, No. 1, pp. 191-211 (1992).

N. G. de Bruijn; "A combinatorial problem,"; Koninklijke Nederlandse Akademie v. Wetenschappen, vol. 49, No. 49, pp. 758-764 (1946).

F. Ruskey, et al.; "De Bruijn sequences for fixed-weight binary strings,"; SIAM Journal on Discrete Mathematics, vol. 26, No. 2, pp. 605-617 (2012).

R. K. Ahuja, et al.; "Network flows: theory, algorithms, and applications."; Prentice Hall (1993).

R. P. Stanley; "Enumerative combinatorics."; Cambridge university press; vol. 1. (2011).

R. Varshamov; "A class of codes for asymmetric channels and a problem from the additive theory of numbers,"; IEEE Trans. Inform. Theory, vol. 19, No. 1, pp. 92-95 (1973).

A. I. Barvinok; "A polynomial time algorithm for counting integral points in polyhedra when the dimension is fixed,"; Mathematics of Operations Research, vol. 19, No. 4, pp. 769-779 (1994).

P. A. Pevzner, et al.; "Towards DNA sequencing chips,"; in Mathematical Foundations of Computer Science 1994. Springer, pp. 143-158 (1994).

S. Tan, et al.; "Sets represented as the length-n factors of a word,"; in Combinatorics on Words; Springer; pp. 250-261 (2013).

K. Heinrich; "Path decompositions,"; Le Matematiche, vol. 47, No. 2, pp. 241-258 (1993).

J. N. Cooper, et al.; "Generalized de Bruijn cycles,"; Annals of Combinatorics, vol. 8, No. 1, pp. 13-25 (2004).

A. Jiang, et al.; "Rank modulation for flash memories,"; IEEE Trans. Inform. Theory; vol. 55, No. 6, pp. 2659-2673 (2009).

A. Barg, et al.; "Codes in permutations and error correction for rank modulation,"; IEEE Trans. Inform. Theory; vol. 56, No. 7, pp. 3158-3165 (2010).

F. Farnoud, et al.; "Error-correction in flash memories via codes in the Ulam metric,"; IEEE Trans. Inform. Theory; vol. 59, No. 5, pp. 3003-3020 (2013).

F. Farnoud, et al.; "Multipermutation codes in the Ulam metric for nonvolatile memories,"; Selected Areas in Communications IEEE Journal on; vol. 32, No. 5, pp. 919-932 (2014).

T. Alderson, et al.; "On maximum Lee distance codes,"; J. of Discrete Mathematics (2013).

J. Astola; "The Theory of Lee-codes,"; Lappeenranta University of Technology, Department of Physics and Mathematics, Research Report (Jan. 1982).

P. Delsarte; "An algebraic approach to the association schemes of coding theory,"; Doctoral dissertation, Universite Catholique de Louvain (1973).

A. Fazeli, et al.; "Generalized Sphere Packing Bound,"; available at http://arxiv.org/abs/1401.6496 (2014).

Feng, J., et al.; "Identification of Single Nucleotides in MoS2 Nanopores,"; arXiv preprint, arXiv:1505.01608 (2015).

R. Feynman; "There's Plenty of Room at the Bottom,"; Caltech, Pasadena; Lecture (Dec. 29, 1959).

E. Hof, et al., "Capacity-achieving polar codes for arbitrarily permuted parallel channels,"; IEEE Trans. on Info. Theory; vol. 59, No. 3, pp. 1505-1516 (Mar. 2013).

M. Kaykobad' "Positive solutions of positive linear systems,"; Lin. Alg. and its App., vol. 64, pp. 133-140 (Jan. 1985).

A.A. Kulkarni, et al.; "Nonasymptotic upper bounds for deletion correcting codes,"; IEEE Trans. on Info. Theory, vol. 59, No. 8, pp. 5115-5130 (Apr. 2013).

A. Mazumdar, et al.; "Coding for high-density recording on a 1-D granular magnetic medium,"; IEEE Trans. on Info. Theory, vol. 57, No. 11, pp. 7403-7417 (Jun. 2011).

T. Richardson, et al.; "The capacity of low-density parity-check codes under message-passing decoding,"; IEEE Trans. on Info. Theory, vol. 47, No. 2, pp. 599-618 (Aug. 2002).

Tal, I., et al.; "How to construct polar codes,"; IEEE Trans. on Info. Theory, vol. 59, No. 10, pp. 6562-6582 (Sep. 2013).

J. Bornholt, et al.; "A dna-based archival storage system,"; Proceedings of the Twenty-First International Conference on Architectural Support for Programming Languages and Operating Systems; ACM, pp. 637-649 (2016).

D. Bajic, et al.; "A simple suboptimal construction of cross-bifix-free codes"; Cryptography and Communications archive 6:27-37 (Aug. 8, 2013).

V. Baldoni, et al.; "A user's guide for LattE integrale v1.7.2"; retrieved from https://www.math.ucdavis.edu/~latte/software/packages/latte_current/manual_v1.7.2.pdf on Mar. 8, 2017; (Oct. 2014).

T. Abualrub, et al.; "Construction of cyclic codes over GF(4) for DNA computing"; Journal of the Franklin Institute, 343, pp. 448-457 (2006).

(56) References Cited

OTHER PUBLICATIONS

D.H. Wood; "Applying error correcting codes to DNA computing (Abstract)"; Proceedings of the 4th DIMACS International Meeting on DNA Based Computing, pp. 109-110 (1998).

M. Hagiwara; "A short proof for the multi-deletion error correction property of Helberg codes,"; IEICE Communications Express, vol. 5, No. 2, pp. 49-51 (Jan. 25, 2016).

O. Milenkovic, et al.; "On the design of codes for DNA computing"; Coding and Cryptography International Workshop, Revised Selected Papers, pp. 100-119 (Mar. 14-18, 2005).

J.I. Hall; "Notes on Coding Theory (Chapter 5—Generalized Reed-Solomon Codes)"; Department of Mathematics, Michigan State University; available online at http://users.math.msu.edu/users/jhall/classes/codenotes/coding-notes.html; (Jan. 7, 2015 revision).

J.I. Hall; "Notes on Coding Theory (Chapter 6—Modifying Codes)"; Department of Mathematics, Michigan State University; available online at http://users.math.msu.edu/users/jhall/classes/codenotes/coding-notes.html; (Jan. 7, 2015 revision).

J.I. Hall; "Notes on Coding Theory (Chapter 7—Codes over Subfields)"; Department of Mathematics, Michigan State University; available online at http://users.math.msu.edu/users/jhall/classes/codenotes/coding-notes.html; (Jan. 7, 2015 revision).

J.I. Hall; "Notes on Coding Theory (Chapter 8—Cyclic Codes)"; Department of Mathematics, Michigan State University; available online at http://users.math.msu.edu/users/jhall/classes/codenotes/coding-notes.html; (Jan. 7, 2015 revision).

J.I. Hall; "Notes on Coding Theory (Chapter 9—Weight and Distance Enumeration)"; Department of Mathematics, Michigan State University; available online at http://users.math.msu.edu/users/jhall/classes/codenotes/coding-notes.html; (Jan. 7, 2015 revision).

Ye et al, Primer-Blast: A tool to design target-specific primers for polymerase chain reaction BMC Bioinformatics, vol. 13, article 134 (Year: 2012).

Shendure et al, Next-generation DNA sequencing Nature Biotechnology vol. 26, pp. 1135-1145 (Year: 2008).

Meunier et al, Recombination Drives the Evolution of GC-Content in the Human Genome Molecular Biology and Evolution, vol. 21, pp. 984-990 (Year: 2004).

J. Brakensiek, et al.; "Efficient low-redundancy codes for correcting multiple deletions,"; arXiv preprint arXiv:1507.06175 (2015).

E. Brill, et al.; "An improved error model for noisy channel spelling correction,"; Proceedings of the 38th Annual Meeting on Association for Computational Linguistics. Association for Computational Linguistics, pp. 286-293 (2000).

D. Cullina, et al.; "An improvement to levenshtein's upper bound on the cardinality of deletion correcting codes,"; IEEE Transactions on Information Theory, vol. 60, No. 7, pp. 3862-3870 (2014).

F. J. Damerau; "A technique for computer detection and correction of spelling errors," Commun. ACM, vol. 7, No. 3, pp. 171-176 Available: http://doi.acm.org/10.1145/363958.363994 (Mar. 1964).

R. Gabrys, et al.; "Graded bit-error-correcting codes with applications to flash memory,"; IEEE Transactions on Information Theory, vol. 59, No. 4, pp. 2315-2327 (2013).

A. S. Helberg, et al.; "On multiple insertion/deletion correcting codes," Information Theory, IEEE Transactions on, vol. 48, No. 1, pp. 305-308 (2002).

S. Kumar, et al.; "Mega3: integrated software for molecular evolutionary genetics analysis and sequence alignment,"; Briefings in bioinformatics, vol. 5, No. 2, pp. 150-163 (2004).

V. I. Levenshtein; "Binary codes capable of correcting deletions, insertions, and reversals," in Soviet physics doklady, vol. 10, No. 8, pp. 707-710 (1966).

F. Paluncic, et al.; "A note on non-binary multiple insertion/deletion correcting codes," in IEEE Information Theory Workshop (2011).

F. Sala, et al.; "Exact reconstruction from insertions in synchronization codes,"; arXiv preprint, arXiv:1604.03000 (2016).

C. Schoeny, et al.; "Codes for correcting a burst of deletions or insertions,"; arXiv preprint, arXiv:1602.06820 (2016).

L. J. Schulman; "Asymptotically good codes correcting insertions, deletions, and transpositions,"; IEEE transactions on information theory, vol. 45, No. 7, pp. 2552-2557 (1999).

N. J. Sloane; "On single-deletion-correcting codes,"; Codes and Designs, de Gruyter, Berlin, pp. 273-291 (2002).

M. M. Vilenchik; "Endogenous dna double-strand breaks: production, fidelity of repair, and induction of cancer,"; Proceedings of the National Academy of Sciences, vol. 100, No. 22, pp. 12871-12876 (2003).

J. Wolf; "On codes derivable from the tensor product of check matrices,"; IEEE Transactions on Information Theory, vol. 11, No. 2, pp. 281-284 (1965).

L.M. Adleman; "Molecular computation of solutions to combinatorial problems,"; Science, vol. 266, pp. 1021-1024 (Nov. 1994).

Y. Benenson, et al.; "An autonomous molecular computer for logical control of gene expression,"; Nature, vol. 429, pp. 423-429 (May 2004).

D. Boneh, et al.; "Breaking DES using a molecular computer,"; Technical Report CS-TR-489-95, Department of Computer Science, Princeton University (1995).

R.S. Braich, et al.; "Solution of a 20-variable 3-SAT problem on a DNA computer,"; Science, vol. 296, pp. 492-502 (Apr. 2002).

K. Breslauer, et al.; "Predicting DNA duplex stability from the base sequence,"; Proc. Natl. Acad. Sci. USA, vol. 83, pp. 3746-3750 (1986).

P. Clote, et al.; "Computational Molecular Biology—an Introduction,"; Wiley Series in Mathematical and Computational Biology, New York (2000).

A. D'yachkov, et al.; "Exordium for DNA codes,"; J. Comb. Optim., vol. 7, No. 4, pp. 369-379 (2003).

A. D'yachkov, et al.; "New results on DNA codes,"; Proc. IEEE Int. Symp. Inform. Theory (ISIT'05), Adelaide, Australia, pp. 283-287 (Sep. 2005).

P. Gaborit, et al.; "Linear constructions for DNA codes,"; Theoretical Computer Science, vol. 334, No. 1-3, pp. 99-113 (Apr. 2005).

C.H. Cooke, et al.; "Polynomial construction of complex Hadamard matrices with cyclic core,"; Applied Mathematics Letters, vol. 12, pp. 87-93 (1999).

O.D. King; "Bounds for DNA codes with constant GC-content,"; The Electronic Journal of Combinatorics, vol. 10, No. 1, #R33 (2003).

M. Mansuripur, et al.; "Information storage and retrieval using macromolecules as storage media,"; University of Arizona Technical Report (2003).

A. Marathe, et al.; "On combinatorial DNA word design,"; J. Comput. Biol., vol. 8, pp. 201-219 (2001).

S. Mneimneh; "Computational Biology Lecture 20: RNA secondary structures,"; available online at engr.smu.edu/»saad/courses/cse8354/lectures/lecture20.pdf.

O. Milenkovic; "On the generalized Hamming weight enumerators and coset weight distributions of even isodual codes,"; Proceedings of the 2001 IEEE International Symposium on Information Theory (Jun. 29, 2001).

O. Milenkovic, et al.; "DNA codes that avoid secondary structures," Proc. IEEE Int. Symp. Inform. Theory (ISIT'05), Adelaide, Australia, pp. 288-292 (Sep. 2005).

R. Nussinov, et al.; "Fast algorithms for predicting the secondary structure of single stranded RNA,"; Proc. Natl. Acad. Sci. USA, vol. 77, No. 11, pp. 6309-6313 (1980).

V. Rykov, et al.; "DNA sequences and quaternary cyclic codes," Proc. IEEE Int. Symp. Inform. Theory (ISIT'01), Washington DC, p. 248 (Jun. 2001).

M.N. Stojanovic, et al.; "A deoxyribozyme-based molecular automaton,"; Nature Biotechnology vol. 21, pp. 1069-1074 (2003).

M. Svanstråom, et al.; "Bounds and constructions for ternary constant-composition codes,"; IEEE Trans. Inform. Theory, vol. 48, No. 1, pp. 101-111 (Jan. 2002).

S. Tsaftaris, et al.; "DNA computing from a signal processing viewpoint,"; IEEE Signal Processing Magazine, pp. 100-106 (Sep. 2004).

K.K. Tzeng, et al.; "On extending Goppa codes to cyclic codes," IEEE Trans. Inform. Theory, vol. IT-21, pp. 712-716 (Nov. 1975).

(56) References Cited

OTHER PUBLICATIONS

E. Winfree, "DNA computing by self-assembly," The Bridge, vol. 33, No. 4, pp. 31-38 (2003); Also available online at http://www.dna.caltech.edu/Papers/FOE 2003 final.pdf.
M. Zuker; "Mfold web server for nucleic acid folding and hybridization prediction,"; Nucleic Acids Res., vol. 31, No. 13, pp. 3406-3415 (2003) Web access at http://www.bioinfo.rpi.edu/»zukerm/rna/.
R. Gabrys, et al.; "Codes in the Damerau Distance for Deletion and Adjacent Transposition Correction"; arXiv:1601.06885, published to arxiv.org on Sep. 6, 2016.
P. T. Gilham, et al.; "Studies on polynucleotides. i. a new and general method for the chemical synthesis of the c5 internucleotidic linkage. syntheses of deoxyribo-dinucleotides1,"; Journal of the American Chemical Society, vol. 80, No. 23, pp. 6212-6222 (1958).
S. Roy, et al.; "Synthesis of dna/rna and their analogs via phosphoramidite and h-phosphonate chemistries,"; Molecules, vol. 18, No. 11, pp. 14 268-14 284 (2013).
C. B. Reese; "Oligo- and poly-nucleotides: 50 years of chemical synthesis,"; Organic & biomolecular chemistry, vol. 3, No. 21, pp. 3851-3868 (2005).
B. C. Froehler, et al. "Synthesis of dna via deoxynudeoside h-phosphonate intermediates,"; Nucleic Acids Research, vol. 14, No. 13, pp. 5399-5407 (1986).
P. J. Garegg, et al.; "Nucleoside h-phosphonates. iii. chemical synthesis of oligodeoxyribonucleotides by the hydrogenphosphonate approach,"; Tetrahedron letters, vol. 27, No. 34, pp. 4051-4054 (1986).
H. Khorana, et al.; "Syntheses of dideoxyribonucleotides,"; Journal of the American Chemical Society, vol. 79, No. 4, pp. 1002-1003 (1957).
R. L. Letsinger, et al.; "Oligonucleotide synthesis on a polymer support1, 2," Journal of the American Chemical Society, vol. 87, No. 15, pp. 3526-3527 (1965).
R. L. Letsinger, et al; "Nucleotide chemistry. xiii. synthesis of oligothymidylates via phosphotriester intermediates,"; Journal of the American Chemical Society, vol. 91, No. 12, pp. 3350-3355 (1969).
R. L. Letsinger, et al.; "Synthesis of thymidine oligonucleotides by phosphite triester intermediates,"; Journal of the American Chemical Society, vol. 98, No. 12, pp. 3655-3661 (1976).
S. Beaucage, et al.; "Deoxynucleoside phosphoramiditesa new class of key intermediates for deoxypolynucleotide synthesis,"; Tetrahedron Letters, vol. 22, No. 20, pp. 1859-1862 (1981).
N. Sinha, et al.; "Polymer support oligonucleotide synthesis xviii1. 2): use of cyanoethyi-n, ndialkylamino-/n-morpholino phosphoramidite of deoxynucleosides for the synthesis of dna fragments simplifying deprotection and isolation of the final product," Nucleic Acids Research, vol. 12, No. 11, pp. 4539-4557 (1984).
S. P. Fodor, et al.; "Light-directed, spatially addressable parallel chemical synthesis,"; Science, vol. 251 (1991).
A. C. Pease, et al.; "Light-generated oligonucleotide arrays for rapid dna sequence analysis,"; Proceedings of the National Academy of Sciences, vol. 91, No. 11, pp. 5022-5026 (1994).
X. Gao, et al.; "In situ synthesis of oligonucleotide microarrays,"; Biopolymers, vol. 73, No. 5, pp. 579-596 (2004).
T. R. Hughes, et al.; "Expression profiling using microarrays fabricated by an ink-jet oligonucleotide synthesizer,"; Nature biotechnology, vol. 19, No. 4, pp. 342-347 (2001).
S. Singh-Gasson, et al.; "Maskless fabrication of light-directed oligonucleotide microarrays using a digital micromirror array,"; Nature biotechnology, vol. 17, No. 10, pp. 974-978 (1999).
E. F. Nuwaysir, et al.; "Gene expression analysis using oligonucleotide arrays produced by maskless photolithography,"; Genome research, vol. 12, No. 11, pp. 1749-1755 (2002).
A. L. Ghindilis, et al.; "Combimatrix oligonucleotide arrays: genotyping and gene expression assays employing electrochemical detection,"; Biosensors and Bioelectronics, vol. 22, No. 9, pp. 1853-1860 (2007).

D. S. Kong, et al.; "Parallel gene synthesis in a microfluidic device,"; Nucleic acids research, vol. 35, No. 8, p. e61, (2007).
E. M. LeProust, et al.; "Synthesis of high-quality libraries of long (150mer) oligonucleotides by a novel depurination controlled process,"; Nucleic acids research, vol. 38, No. 8, pp. 2522-2540 (2010).
L.-C. Au, et al.; "Gene synthesis by a lcr-based approach: High-level production of leptin-I54 using synthetic gene *Enescherichia coli*,"; Biochemical and biophysical research communications, vol. 248, No. 1, pp. 200-203 (1998).
W. P. Stemmer, et al.; "Single-step assembly of a gene and entire plasmid from large numbers of oligodeoxyribonucleotides,"; Gene, vol. 164, No. 1, pp. 49-53 (1995).
D. G. Gibson; "Synthesis of dna fragments in yeast by one-step assembly of overlapping oligonucleotides,"; Nucleic acids research, p. gkp687 (2009).
D. G. Gibson, et al.; "Chemical synthesis of the mouse mitochondrial genome,"; nature methods, vol. 7, No. 11, pp. 901-903 (2010).
J. Tian, et al.; "Accurate multiplex gene synthesis from programmable dna microchips,"; Nature, vol. 432, No. 7020, pp. 1050-1054 (2004).
A. Y. Borovkov, et al.; "Highquality gene assembly directly from unpurified mixtures of microarraysynthesized oligonucleotides,"; Nucleic acids research, vol. 38, No. 19, pp. e180-e180 (2010).
S. Kosuri, et al.; "Scalable gene synthesis by selective amplification of dna pools from high-fidelity microchips,"; Nature biotechnology, vol. 28, No. 12, pp. 1295-1299 (2010).
J. Quan, et al.; "Parallel on-chip gene synthesis and application to optimization of protein expression,"; Nature biotechnology, vol. 29, No. 5, pp. 449-452 (2011).
P. A. Carr, et al.; "Protein-mediated error correction for de novo dna synthesis,"; Nucleic acids research, vol. 32, No. 20, pp. e162-e162 (2004).
B. F. Binkowski, et al.; "Correcting errors in synthetic dna through consensus shuffling,"; Nucleic acids research, vol. 33, No. 6, pp. e55-e55 (2005).
W. Wan, et al.; "Error removal in microchip-synthesized dna using immobilized muts,"; Nucleic acids research, p. gku405 (2014).
J. Smith, et al.; "Removal of polymerase-produced mutant sequences from pcr products,"; Proceedings of the National Academy of Sciences, vol. 94, No. 13, pp. 6847-6850 (1997).
M. Fuhrmann, et al.; "Removal of mismatched bases from synthetic genes by enzymatic mismatch cleavage,"; Nucleic acids research, vol. 33, No. 6, pp. e58-e58 (2005).
B. J. Till, et al.; "Mismatch cleavage by single-strand specific nucleases,"; Nucleic Acids Research, vol. 32, No. 8, pp. 2632-2641 (2004).
C. A. Oleykowski, et al.; "Mutation detection using a novel plant endonuclease,"; Nucleic acids research, vol. 26, No. 20, pp. 4597-4602 (1998).
I. Saaem, et al.; "Error correction of microchip synthesized genes using surveyor nuclease,"; Nucleic acids research, p. gkr887 (2011).
P. R. Dormitzer, et al.; "Synthetic generation of influenza vaccine viruses for rapid response to pandemics,"; Science translational medicine, vol. 5, No. 185, pp. 185ra68-185ra68 (2013).
M. Matzas, et al.; "Highfidelity gene synthesis by retrieval of sequence-verified dna identified using high-throughput pyrosequencing,"; Nature biotechnology, vol. 28, No. 12, pp. 1291-1294 (2010).
H. Lee, et al.; "A high-throughput optomechanical retrieval method for sequence-verified clonal dna from the ngs platform,"; Nature communications, vol. 6 (2015).
H. Kim, et al.; "'shotgun dna synthesis' for the high-throughput construction of large dna molecules,"; Nucleic acids research, p. gks546 (2012).
J. J. Schwartz, et al.; "Accurate gene synthesis with tag-directed retrieval of sequence-verified dna molecules,"; Nature methods, vol. 9, No. 9, pp. 913-915 (2012).
R. Higuchi, et al.; "A general method of in vitro preparation and specific mutagenesis of dna fragments: study of protein and dna interactions,"; Nucleic acids research, vol. 16, No. 15, pp. 7351-7367 (1988).
R. Jansen, et al.; "Identification of genes that are associated with dna repeats in prokaryotes,"; Molecular microbiology, vol. 43, No. 6, pp. 1565-1575 (2002).

(56) References Cited

OTHER PUBLICATIONS

F. Sanger, et al.; "DNA sequencing with chainterminating inhibitors,"; Proc. Natl. Acad. Sci. U.S.A., vol. 74, No. 12, pp. 5463-5467 (Dec. 1977).
E. S. Lander, et al.; "Initial sequencing and analysis of the human genome,"; Nature, vol. 409, No. 6822, pp. 860-921 (Feb. 2001).
R. H. Waterston, et al.; "Initial sequencing and comparative analysis of the mouse genome,"; Nature, vol. 420, No. 6915, pp. 520-562 (Dec. 2002).
D. A. Wheeler, et al.; "The complete genome of an individual by massively parallel DNA sequencing,"; Nature, vol. 452, No. 7189, pp. 872-876 (Apr. 2008).
P. A. Pevzner, et al.; "An Eulerian path approach to DNA fragment assembly,"; Proc. Natl. Acad. Sci. U.S.A., vol. 98, No. 17, pp. 9748-9753 (Aug. 2001).
Alon, et al., "Simple constructions of almost k-wise independent random variables," Random Structures & Algorithms, vol. 3, No. 3, pp. 289-304, 1992.
Batu, et al., "Reconstructing strings from random traces," in Proceedings of the 15th Annual ACM-SIAM Symposium on Discrete Algorithms (SODA), 2004, pp. 910-918.
Bertalmio et al., "Image Inpainting", in Proceedings of the 27th annual conference on Computer graphics and interactive techniques. ACM Press/Addison-Wesley Publishing Co., 2000, pp. 417-424.
Haeupler et al., "Repeated deletion channels," in 2014 IEEE Information Theory Workshop (ITW), Nov. 2014, pp. 152-156.
Holenstein, et al., "Trace reconstruction with constant deletion probability and related results," in Proceedings of the 19th Annual ACM-SIAM Symposium on Discrete Algorithms (SODA), 2008, pp. 389-398.
Huffman, "A Method for the Construction of Minimum-Redundancy Codes", Proceedings of the I.R.E., Sep. 1952, pp. 1098-1101.
Kumar and Milenkovic, "On Unequal Error Protection LDPC Codes Based on Plotkin-Type Constructions", IEEE Transactions on Communication, vol. 54, No. 6, Jun. 2006, pp. 994-1005.
Levenshtein, "Efficient reconstruction of sequences," IEEE Transactions on Information Theory, vol. 47, No. 1, pp. 2-22, Jan. 2001.
Magner, et al, "Fundamental bounds for sequence reconstruction from nanopore sequencers," IEEE Transactions on Molecular, Biological and Multi-Scale Communications, vol. 2, No. 1, pp. 92-106, Jun. 2016.
McGregor, et al., "Trace reconstruction revisited," in Algorithms—ESA 2014, A. S. Schulz and D. Wagner, Eds. Berlin, Heidelberg: Springer Berlin Heidelberg, 2014, pp. 689-700.
Milenkovic, et al.; "On the design of codes for DNA computing"; Coding and Cryptography International Workshop, Revised Selected Papers, pp. 100-119 (Mar. 14-18, 2005).
Moon, et al., "Analysis of the clustering properties of the Hilbert space-filling curve," in IEEE Transactions on Knowledge and Data Engineering, vol. 13, No. 1, pp. 124-141, Jan.-Feb. 2001, doi: 10.1109/69.908985.
Nazeri et al., "EdgeConnect: Generative Image Inpainting with Adversarial Edge Learning", https://github.com/knazeri/edge-connect; pp. 1-17, 2019.
Notice of Allowance, U.S. Appl. No. 15/356,118, mailed Sep. 16, 2019.
Office Action, U.S. Appl. No. 15/356,118, mailed May 3, 2019.
Office Action, U.S. Appl. No. 15/356,118, mailed Jul. 19, 2019.
Office Action, U.S. Appl. No. 17/102,143, mailed Feb. 17, 2023.
Organick, et al., "Random access in large-scale DNA data storage," Nature biotechnology, vol. 36, No. 3, p. 242, 2018.
Peres et al, "Average-case reconstruction for the deletion channel: subpolynomially many traces suffice," arXiv e-prints, p. arXiv:1708.00854, Aug. 2017.
Schouhamer Immink et al., "Very efficient balanced codes," IEEE Journal on Selected Areas in Communications, vol. 28, No. 2, pp. 188-192, Feb. 2010.
Shinkar, et al., "Clustering-correcting codes," arXiv e-prints, p. arXiv: 1903.04122, Mar. 2019.
Shomorony et al, "Capacity results for the noisy shuffling channel," arXiv e-prints, p. arXiv:1902.10832, Feb. 2019.
Song, et al., "Sequence-subset distance and coding for error control in DNA-based data storage," arXiv e-prints, p. arXiv:1809.05821, Sep. 2018.
Srinivasavaradhan, et al, "On maximum likelihood reconstruction over multiple deletion channels," in 2018 IEEE International Symposium on Information Theory (ISIT), Jun. 2018, pp. 436-440.
Tabatabaei et al., "DNA punch cards for storing data on native DNA sequences via enzymatic nicking". Nature Communications (2020) 11:17:1742 https://doi.org/10.1038/ s41467-020-15588-z www.nature.com/naturecommunications.
Tabatabaei Yazdi, et al, "Mutually uncorrelated primers for DNA-based data storage," IEEE Transactions on Information Theory, vol. 64, No. 9, pp. 6283-6296, Sep. 2018.
Tomasi and Manduchi, "Bilateral Filtering for Gray and Color Images", Proceeding of the 1998 IEEE International Conference on Computer Vision, Bombay, India, 8 pages.
Yazdi et al., "Portable and Error-Free DNA-Based Data Storage", Scientific Reports, www.nature.com/scientificreports, 7:5011 DOI:10.1038/s41598-017-05188-1 (2017).
Zhirnov et al., Nucleic Acid Memory, Nat. Mater. Apr. 2016; 15(4):366-370. doi:10.1038/nmat4594.
Notice of Allowance, U.S. Appl. No. 17/102,143, mailed May 4, 2023.
Office Action, U.S. Appl. No. 17/069,247, mailed Oct. 5, 2023.

\* cited by examiner

Example set of address primers that satisfy three constraints

Unacceptable set of address primers because they don't exhibit 50% GC content

Unacceptable set of address primers because they are not *k*-mutually uncorrelated and they do not have sufficient Hamming distance from one another Example set of address primers that satisfy all three constraints and share a common concluding base

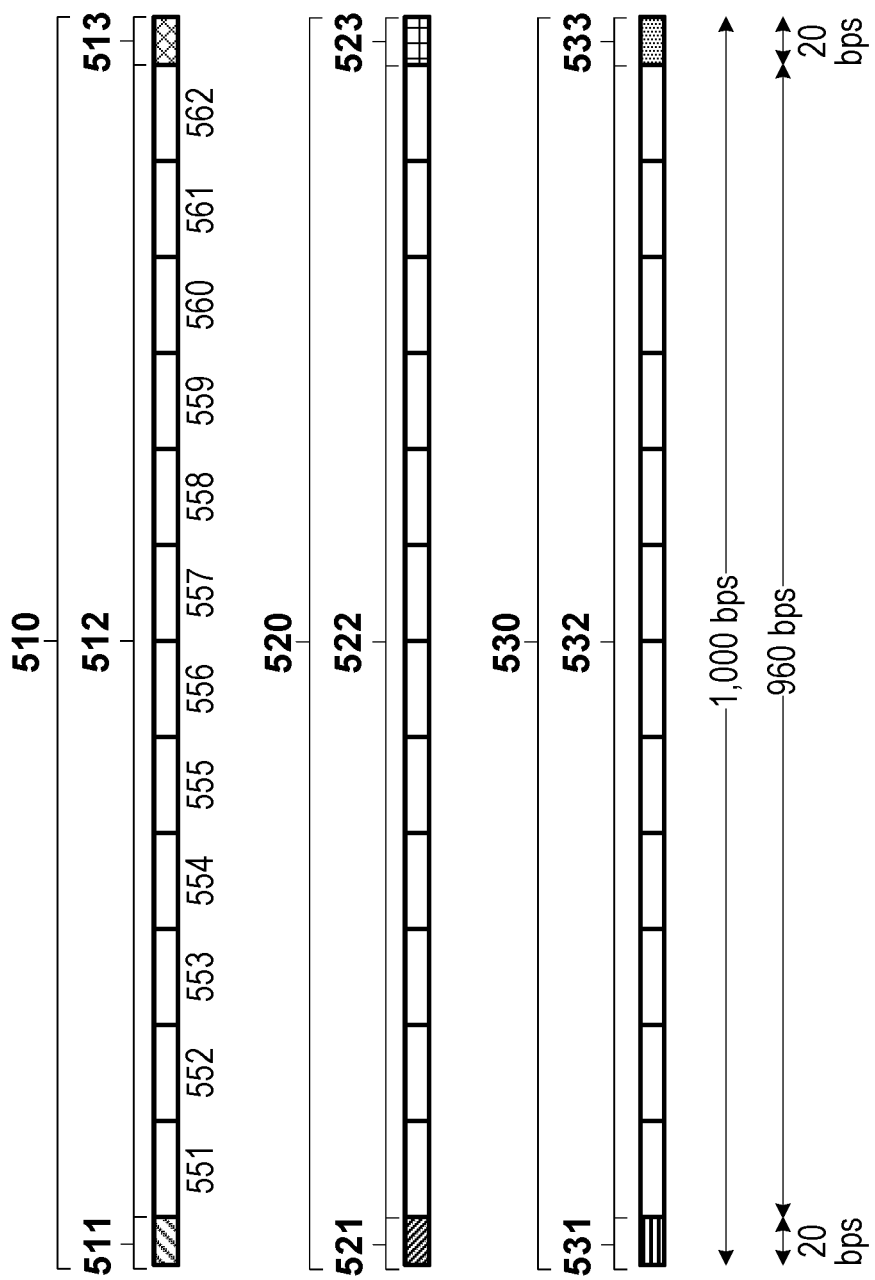

gBlock based method

OE-PCR based method

SEQUENCE LISTING

```
<160> NUMBER OF SEQ ID NOS: 22

<210> SEQ ID NO 1
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 1
gtattgccag ag                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 2
tcccatgaga ga                                                          12

<210> SEQ ID NO 3
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 3
acggccttct ta                                                          12

<210> SEQ ID NO 4
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 4
ggatcgccag cg                                                          12

<210> SEQ ID NO 5
<211> LENGTH: 12
<212> TYPE: DNA
```

```
<213> ORGANISM: Artificial Sequence
<220> FEATURE:
<223> OTHER INFORMATION: Synthetic oligonucleotide

<400> SEQUENCE: 5
ccgcgctggc ga                                                              12

<210> SEQ ID NO 6
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 6
tgcgcctccc gc                                                              12

<210> SEQ ID NO 7
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 7
cataccgtct tg                                                              12

<210> SEQ ID NO 8
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 8
gagaccgtca ta                                                              12

<210> SEQ ID NO 9
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 9
catagcgcca ta                                                              12

<210> SEQ ID NO 10
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 10
actactctca cg                                                              12

<210> SEQ ID NO 11
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 11
ctccactcat ag                                                              12
```

```
<210> SEQ ID NO 12
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 12
tactccaacc tg                                                          12

<210> SEQ ID NO 13
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 13 acatgcata                                                               9

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cgtagtcagc gtgtcaatca                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tgcacagtcg agctatcaca                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
gactgactga tgacgactga                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gctatatgcg agtcgagtca                                                  20

<210> SEQ ID NO 18
<211> LENGTH: 20
<212> TYPE: DNA
<213> ORGANISM: Artificial Sequence
<220> FEATURE:
```

```
<223> OTHER INFORMATION: Synthetic oligonucleotide

<400> SEQUENCE: 18
gtacactcag catcgactca                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
aattactaag cgaccttctc                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
agtaagtctc gcagtcatcg                                               20

<210> SEQ ID NO 21
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 21
agtaagtctc gcagtc                                                   16

<210> SEQ ID NO 22
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 22
agtaatcggt ccagtc                                                   16
```

RE-WRITABLE DNA-BASED DIGITAL STORAGE WITH RANDOM ACCESS

CROSS-REFERENCE TO RELATED APPLICATIONS

This application is a continuation of and claims priority to U.S. patent application Ser. No. 15/356,118, filed Nov. 18, 2016, which is hereby incorporated by reference in its entirety.

U.S. patent application Ser. No. 15/356,118 claims priority to U.S. provisional patent application No. 62/257,273, filed Nov. 19, 2015, which is also hereby incorporated by reference in its entirety.

STATEMENT REGARDING FEDERALLY SPONSORED RESEARCH OR DEVELOPMENT

This invention was made with government support under STC Class 2010 CCF 0939370 awarded by National Science Foundation. The government has certain rights in the invention.

SEQUENCE LISTING

The sequence listing submitted herewith, entitled "16-1614-CON_SequenceListing_ST25.txt" and 5 kb in size, is incorporated by reference in its entirety.

BACKGROUND

As the amount of data created every day continues to increase, there is an ongoing need for reliable, high-density storage systems. Deoxyribonucleic acid (DNA) based storage systems offer the possibility of achieving these goals— DNA can maintain a stable configuration for thousands of years and can be used to encode terabytes of data per gram, or more. While DNA-based storage systems have been successfully demonstrated, such systems are limited. For instance, by their very design, these systems do not allow random access, and thus files stored in this fashion can only be read as a whole.

SUMMARY

The embodiments herein provide methods, devices, and systems for rewritable DNA-based storage that allows random access. A DNA sequence that encodes digital information is arranged in blocks of base pairs, including two unique but different address sequences at each end, and uses the remaining base pairs for encoding data. The address sequences are designed to be highly suitable for random access (e.g., mutually uncorrelated and at a large Hamming distance from one another, among other properties). Thus, it is unlikely for one address to be confused with another.

Further, the data appearing between the two addresses of each block is encoded to avoid the appearance of any of the addresses, sufficiently long substrings of the addresses, or substrings similar to the addresses. To achieve this goal, prefix-synchronized encoding schemes are generalized to accommodate multiple sequence avoidance.

Once data is encoded in this fashion, the blocks are combined together in a DNA "soup." In order to read data from a specific block therein, the block's address is identified by a primer corresponding to its address, polymerase chain reaction (PCR) amplified, sequenced, and then decoded. Since the amplification step replicates the block in an exponential fashion, the vast majority of the DNA in the soup will be copies of the block. Then, with exceptionally high probability, any DNA block selected from the soup will contain the data associated with the target address. After a block is selected in this fashion, it may either be replaced by a newly synthesized DNA block containing the same addresses and new data, or it may be changed by a DNA editing technique.

Particularly, a first example embodiment may involve a method. The method includes selecting address representations of m nucleotide sequences of n bases each. Each of the address representations of m nucleotide sequences (i) consists of approximately 50% guanine and cytosine content and (ii) is self-uncorrelated. The address representations are mutually uncorrelated with one another. All of the address representations end with a particular base. The method also includes selecting, for a particular address representation from the address representations of the m nucleotide sequences, a corresponding data representation of a nucleotide sequence of L bases. The data representation encodes an integer value less than $3^L$ that is a sum of a first addend and a second addend. The data representation includes a first subsequence of bases encoding the first addend followed by a second subsequence of bases encoding the second addend. The first addend is encoded based on mappings of subvalues of the first addend to n sets of bases respectively associated with the n bases of the particular address representation. The second subsequence of bases is a ternary encoding of the second addend over a set of three bases not including the particular base. The data representation is uncorrelated with each of the address representations. Further, the method includes concatenating the particular address representation with the data representation to form a representation of a target nucleotide sequence of n+L bases. The method additionally includes synthesizing the target nucleotide sequence.

A second example embodiment may involve a method. The method includes reading a nucleotide sequence of 2n+L bases to form a representation of the nucleotide sequence. The method also includes dividing the representation of the nucleotide sequence into an address representation of n bases, followed by a data representation of L bases, followed by a further address representation of n bases. The address representation and the further address representation are each uncorrelated with one another, self-uncorrelated, and end with a particular base. Further, the method includes decoding the data representation into an integer value less than $3^L$ that is a sum of a first addend and a second addend. The data representation includes a first subsequence of bases encoding the first addend followed by a second subsequence of bases encoding the second addend. The first addend is encoded based on mappings of subvalues of the first addend to n sets of bases respectively associated with the n bases of the address representation. The second subsequence of bases is a ternary encoding of the second addend over a set of three bases not including the particular base. The data representation is uncorrelated with each of the address representations.

A third example embodiment may involve a method. The method includes a means for selecting address representations of m nucleotide sequences of n bases each. Each of the address representations of m nucleotide sequences (i) consists of approximately 50% guanine and cytosine content and (ii) is self-uncorrelated. The address representations are mutually uncorrelated with one another. All of the address representations end with a particular base. The method also includes a means for selecting, for a particular address representation from the address representations of the m nucleotide sequences, a corresponding data representation of a nucleotide sequence of L bases. The data representation encodes an integer value less than $3^L$ that is a sum of a first addend and a second addend. The data representation includes a first subsequence of bases encoding the first addend followed by a second subsequence of bases encoding the second addend. The first addend is encoded based on mappings of subvalues of the first addend to n sets of bases respectively associated with the n bases of the particular address representation. The second subsequence of bases is a ternary encoding of the second addend over a set of three bases not including the particular base. The data representation is uncorrelated with each of the address representations. Further, the method includes a means for concatenating the particular address representation with the data representation to form a representation of a target nucleotide sequence of n+L bases. The method additionally includes a means for synthesizing the target nucleotide sequence.

These as well as other embodiments, aspects, advantages, and alternatives will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

FIG. 5A illustrates multiple data blocks within a set of data blocks, according to example embodiments.

DETAILED DESCRIPTION

Example methods, devices, media, and systems are described herein. Other embodiments can be utilized, and other changes can be made, without departing from the scope of the subject matter presented herein. Thus, these example embodiments are not meant to be limiting. It will be readily understood that the aspects of the present disclosure, as generally described herein, and illustrated in the figures, can be arranged, substituted, combined, separated, and designed in a wide variety of different configurations, all of which are contemplated herein.

As used herein, the words "example" and "exemplary" mean "serving as an example, instance, or illustration." Any embodiment or feature described herein as being an "example" or "exemplary" is not necessarily to be construed as preferred or advantageous over other embodiments or features. The term "optimization" as used herein should not be interpreted to require that the "optimal" or "best" solution to any problem is found. Instead, "optimization" refers to a process through which better results may be obtained.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

Regardless of how they may be implemented, the embodiments herein may make use of one or more computing devices. These computing devices may include, for example, client devices under the control of users, and server devices that directly or indirectly interact with the client devices. Such devices are described in the following section.

1. EXAMPLE COMPUTING DEVICES AND CLOUD-BASED COMPUTING ENVIRONMENTS

Figure 1:
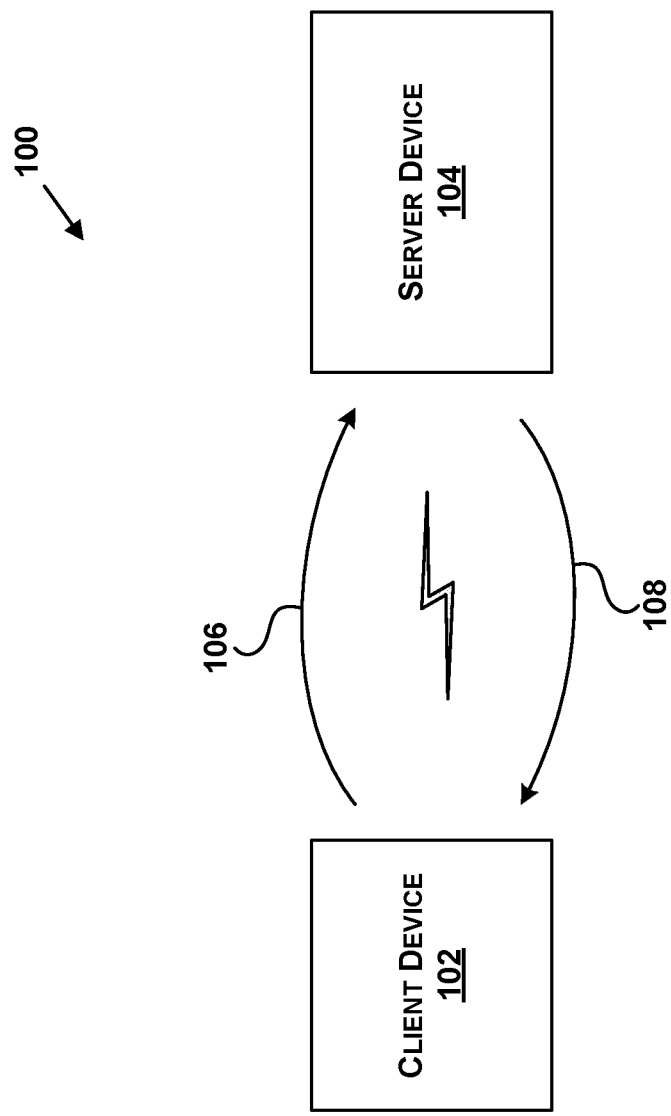
FIG. 1 is a high-level depiction of a client-server computing system, according to example embodiments.

FIG. 1 illustrates an example communication system 100 for carrying out one or more of the embodiments described herein. Communication system 100 may include computing devices. Herein, a "computing device" may refer to either a client device, a server device (e.g., a stand-alone server computer or networked cluster of server equipment), or some other type of computational platform.

Client device 102 may be any type of device including a personal computer, laptop computer, a wearable computing device, a wireless computing device, a head-mountable computing device, a mobile telephone, or tablet computing device, etc., that is configured to transmit data 106 to and/or receive data 108 from a server device 104 in accordance with the embodiments described herein. For example, in FIG. 1, client device 102 may communicate with server device 104 via one or more wireline or wireless interfaces. In some cases, client device 102 and server device 104 may communicate with one another via a local-area network. Alternatively, client device 102 and server device 104 may each reside within a different network, and may communicate via a wide-area network, such as the Internet.

Client device 102 may include a user interface, a communication interface, a main processor, and data storage (e.g., memory). The data storage may contain instructions executable by the main processor for carrying out one or more operations relating to the data sent to, or received from, server device 104. The user interface of client device 102 may include buttons, a touchscreen, a microphone, and/or any other elements for receiving inputs, as well as a speaker, one or more displays, and/or any other elements for communicating outputs.

Server device 104 may be any entity or computing device arranged to carry out the server operations described herein. Further, server device 104 may be configured to send data 108 to and/or receive data 106 from the client device 102.

Data 106 and data 108 may take various forms. For example, data 106 and 108 may represent packets transmitted by client device 102 or server device 104, respectively, as part of one or more communication sessions. Such a communication session may include packets transmitted on a signaling plane (e.g., session setup, management, and teardown messages), and/or packets transmitted on a media plane (e.g., text, graphics, audio, and/or video data).

Regardless of the exact architecture, the operations of client device 102, server device 104, as well as any other operation associated with the architecture of FIG. 1, can be carried out by one or more computing devices. These computing devices may be organized in a standalone fashion, in cloud-based (networked) computing environments, or in other arrangements.

Figure 2:
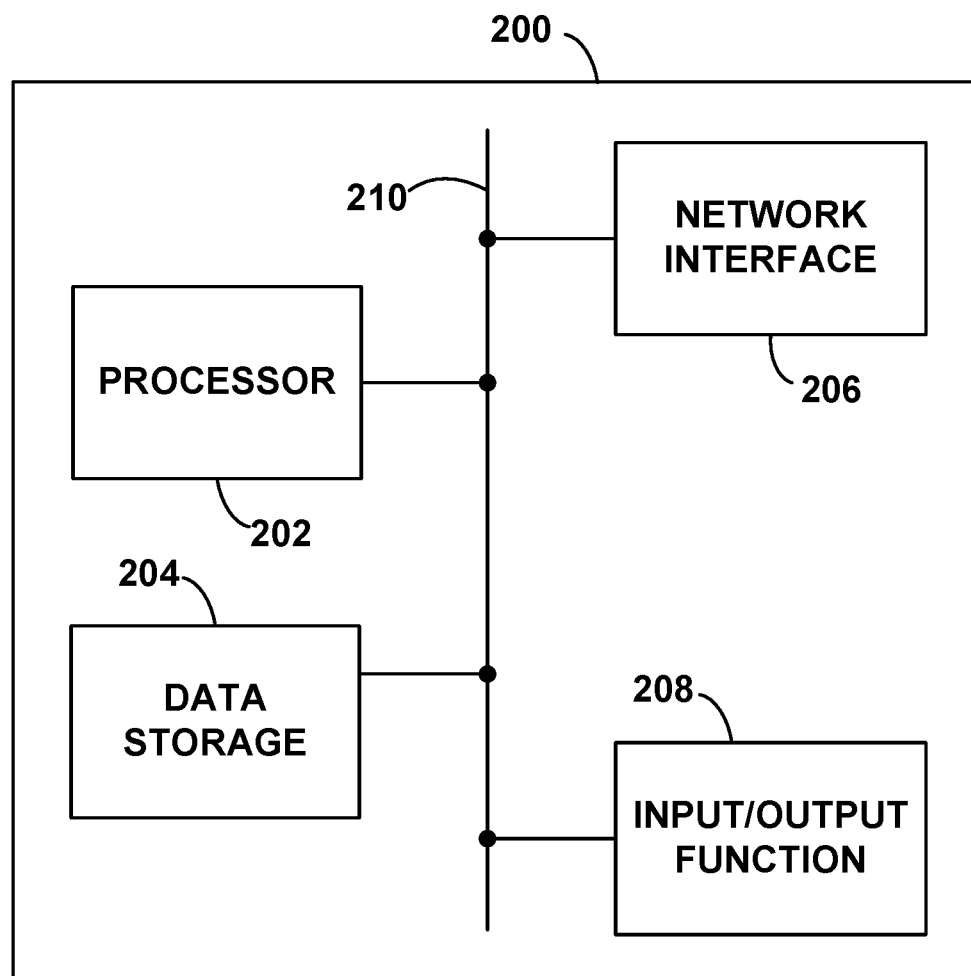
FIG. 2 illustrates a schematic drawing of a computing device, according to example embodiments.

FIG. 2 is a simplified block diagram exemplifying a computing device 200, illustrating some of the functional components that could be included in a computing device arranged to operate in accordance with the embodiments herein. Example computing device 200 could be a client device, a server device, or some other type of computational platform. For purpose of simplicity, this specification may equate computing device 200 to a server from time to time. Nonetheless, the description of computing device 200 could apply to any component used for the purposes described herein.

In this example, computing device 200 includes a processor 202, a data storage 204, a network interface 206, and an input/output function 208, all of which may be coupled by a system bus 210 or a similar mechanism. Processor 202 can include one or more CPUs, such as one or more general purpose processors and/or one or more dedicated processors (e.g., application specific integrated circuits (ASICs), digital signal processors (DSPs), network processors, etc.).

Data storage 204, in turn, may comprise volatile and/or non-volatile data storage and can be integrated in whole or in part with processor 202. Data storage 204 can hold program instructions, executable by processor 202, and data that may be manipulated by these instructions to carry out the various methods, processes, or operations described herein. Alternatively, these methods, processes, or operations can be defined by hardware, firmware, and/or any combination of hardware, firmware and software. By way of example, the data in data storage 204 may contain program instructions, perhaps stored on a non-transitory, computer-readable medium, executable by processor 202 to carry out any of the methods, processes, or operations disclosed in this specification or the accompanying drawings.

Network interface 206 may take the form of a wireline connection, such as an Ethernet, Token Ring, or T-carrier connection. Network interface 206 may also take the form of a wireless connection, such as IEEE 802.11 (Wifi), BLUETOOTH®, or a wide-area wireless connection. However, other forms of physical layer connections and other types of standard or proprietary communication protocols may be used over network interface 206. Furthermore, network interface 206 may comprise multiple physical interfaces.

Input/output function 208 may facilitate user interaction with example computing device 200. Input/output function 208 may comprise multiple types of input devices, such as a keyboard, a mouse, a touch screen, and so on. Similarly, input/output function 208 may comprise multiple types of output devices, such as a screen, monitor, printer, or one or more light emitting diodes (LEDs). Additionally or alternatively, example computing device 200 may support remote access from another device, via network interface 206 or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 3:
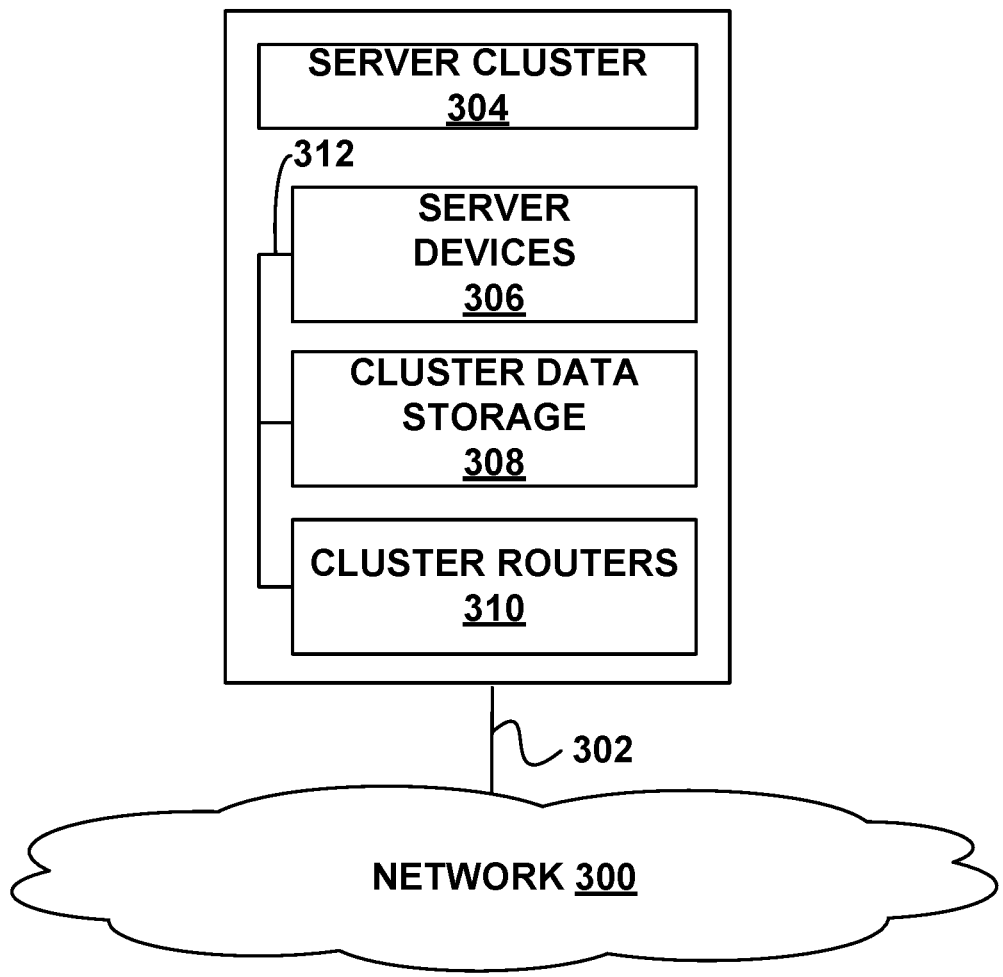
FIG. 3 illustrates a schematic drawing of a networked server cluster, according to example embodiments.

FIG. 3 depicts a cloud-based server cluster 304 in accordance with an example embodiment. In FIG. 3, functions of a server device, such as server device 104 (as exemplified by computing device 200) may be distributed between server devices 306, cluster data storage 308, and cluster routers 310, all of which may be connected by local cluster network 312. The number of server devices, cluster data storages, and cluster routers in server cluster 304 may depend on the computing task(s) and/or applications assigned to server cluster 304.

For example, server devices 306 can be configured to perform various computing tasks of computing device 200. Thus, computing tasks can be distributed among one or more of server devices 306. To the extent that these computing tasks can be performed in parallel, such a distribution of tasks may reduce the total time to complete these tasks and return a result. For purpose of simplicity, both server cluster 304 and individual server devices 306 may be referred to as "a server device." This nomenclature should be understood to imply that one or more distinct server devices, data storage devices, and cluster routers may be involved in server device operations.

Cluster data storage 308 may be data storage arrays that include disk array controllers configured to manage read and write access to groups of hard disk drives. The disk array controllers, alone or in conjunction with server devices 306, may also be configured to manage backup or redundant copies of the data stored in cluster data storage 308 to protect against disk drive failures or other types of failures that prevent one or more of server devices 306 from accessing units of cluster data storage 308.

Cluster routers 310 may include networking equipment configured to provide internal and external communications for the server clusters. For example, cluster routers 310 may include one or more packet-switching and/or routing devices configured to provide (i) network communications between server devices 306 and cluster data storage 308 via cluster network 312, and/or (ii) network communications between the server cluster 304 and other devices via communication link 302 to network 300.

Additionally, the configuration of cluster routers 310 can be based at least in part on the data communication requirements of server devices 306 and cluster data storage 308, the latency and throughput of the local cluster networks 312, the latency, throughput, and cost of communication link 302, and/or other factors that may contribute to the cost, speed, fault-tolerance, resiliency, efficiency and/or other design goals of the system architecture.

As a possible example, cluster data storage 308 may include any form of database, such as a structured query language (SQL) database. Various types of data structures may store the information in such a database, including but not limited to tables, arrays, lists, trees, and tuples. Furthermore, any databases in cluster data storage 308 may be monolithic or distributed across multiple physical devices.

Server devices 306 may be configured to transmit data to and receive data from cluster data storage 308. This transmission and retrieval may take the form of SQL queries or other types of database queries, and the output of such queries, respectively. Additional text, images, video, and/or audio may be included as well. Furthermore, server devices 306 may organize the received data into web page representations. Such a representation may take the form of a markup language, such as the hypertext markup language (HTML), the extensible markup language (XML), or some other standardized or proprietary format. Moreover, server devices 306 may have the capability of executing various types of computerized scripting languages, such as but not limited to Perl, Python, PHP Hypertext Preprocessor (PHP), Active Server Pages (ASP), JavaScript, and so on. Computer program code written in these languages may facilitate the providing of web pages to client devices, as well as client device interaction with the web pages.

2. EXAMPLE DNA STRUCTURE AND SEQUENCING

Genetic sequencing may involve determining the order of nucleotides in a biological sample, such as a block of DNA or RNA. Each nucleotide contains one base structure (or nucleobase) which may be adenine (A), guanine (G), cytosine (C), or thymine (T) for DNA. In RNA, thymine bases are replaced by uracil (U) bases. RNA can be divided into multiple categories, two of which are messenger RNA (mRNA) and micro RNA (miRNA). Messenger RNA includes RNA molecules that are transcribed from a DNA template and that convey genetic information from DNA to a ribosome, where they specify amino acid sequences. Micro RNA includes non-coding RNA molecules (usually containing about 17-25 nucleotides) and can regulate gene expression.

A strand of DNA or RNA may include tens, hundreds, thousands, millions, or billions of nucleotides in a particular ordering. Complete DNA sequences, or genomes, of various organisms have been discovered via a group of techniques generically referred to as "sequencing." Rather than attempting to sequence an entire genome in a monolithic operation, relatively short blocks of DNA or RNA (e.g., a few hundred or a few thousand nucleotides) may be sequenced individually. The sequencing of the individual blocks may involve steps of amplification and electrophoresis.

In order to sequence RNA, complementary DNA (cDNA) for single-strand RNA may be made, and the steps below may take place on the resultant DNA. However, other RNA sequencing techniques are possible, and the embodiments herein do not require the example sequencing technique below to be used.

Amplification refers to the copying of a block of DNA. Various amplification techniques may be used to make multiple copies of such a block from a small initial sample. For instance, PCR is an amplification technique that can rapidly produce thousands of copies of a block.

Using PCR, the block containing the DNA sequencing target, primers (short single-stranded DNA fragments containing subsequences that are complimentary to the sequencing target), free nucleotides, and a polymerase are placed in a thermal cycler. Therein, the sequencing target undergoes one or more cycles of denaturation, annealing, and extension.

In the denaturation phase, the thermal cycler is set to a high temperature, which breaks the hydrogen bonds between bases of the sequencing target. The results are two complementary single-stranded DNA molecules. In the annealing phase, the thermal cycler is set to a lower temperature, which allows bonding of the primers to the single-stranded molecules. Once the primers are bonded to the appropriate locations of the single-stranded molecules, the extension phase begins. The thermal cycler is set to an intermediate temperature (e.g., a temperature between those used in the denaturation and annealing phases), and the polymerase binds complementary free nucleotides along the single-stranded molecules, effectively creating a copy of the original two-stranded DNA sequencing target.

These three phases repeat any number of times, creating an exponentially-growing number of copies of the original sequencing target. For example, in only a few hours, one million or more copies of the original sequencing target may be produced.

An initially popular method of DNA sequence was the Sanger sequencing method. In order to facilitate sequencing the original sequencing target by this method, dideoxynucleotides (ddNTPs) are added to the free nucleotides. A ddNTP has the same chemical structure as the free nucleotides, but is missing a hydroxyl group at the 3' position (e.g., at the end of the molecule to which DNA polymerase incorporates the subsequent nucleotide). Consequently, if a ddNTP is incorporated into a growing complementary strand during the extension phase, it may act as a polymerase inhibitor because the missing hydroxyl group prevents the strand from being elongated. Because the incorporation of ddNTPs is random, when the polymerization process iterates, DNA strands identical to the original sequencing target, but of different lengths, may be produced. If enough polymerization iterations take place for an original sequencing target of n base pairs, new copies of lengths 1 through n may be produced, each terminating with a ddNTP.

The DNA strands can be observed by radiolabeling the probe and resolving each of various lengths using electrophoresis. Alternatively, the ddNTPs for each types of base (e.g., A, C, G, and T) may be fluorescently-labeled with different dyes (colors) that emit light at different wavelengths. Thus, the A ddNTPs may have one color, the C ddNTPs may have another color, and so on. This enables the use of capillary electrophoresis to separate and detect the DNA strands based on size.

In electrophoresis, the replicated sequencing targets are placed in a conductive gel (e.g., polyacrylamide). The gel is subject to an electric field. For instance, a negatively-charged anode may be placed on one side of the gel and a positively-charged cathode may be placed on the other. Since DNA is negatively charged, the sequencing targets (i.e., the elongated strands) can be introduced to the gel near the anode, and they will migrate toward the cathode. Particularly, the shorter the sequencing target, the faster and further it will migrate. After some period of time, the sequencing targets may be arranged in order of decreasing length, with longer sequencing targets near the anode and shorter sequencing targets near the cathode. Similarly, fluorescently-labeled DNA strands by resolved and detected using capillary electrophoresis.

For fluorescently-labeled DNA strands, since the terminating nucleotide of each block is a colored ddNTP, computer imaging can be used to determine the sequence of nucleotides by scanning the colored ddNTP in each sequencing targets from those near the cathode to those near the anode. Alternatively, the colored ddNTP incorporated into each block can be identified as each block migrates past a fixed detector based on its size. By reading the ordered fluorescent molecules, the computer can provide a sequence of nucleotides represented as strings of bases in letter form (e.g., ACATGCATA; SEQ ID NO:13).

The techniques described herein, however, are not limited by the type of sequencing. To that point, advances in computer processing and storage technologies have led to so-called "next-generation sequencing" techniques. While next-generation sequencing may include various procedures, in general they involve use of massively parallel computing to speed the sequencing process. For example, rather than processing sequenced DNA block one at a time, millions of such sequencing targets may be processed in parallel.

3. EXAMPLE ADDRESS DESIGN

Herein below, the terms "address primers" and "address sequences" may be used interchangeably, and may be meant to represent similar concepts. Because an "address sequence" may be treated as a "primer" when selecting a corresponding data sequence during a reading process (e.g., when cutting DNA at a specific location to read the data that follows the primer), "address sequences" also represent "address primers."

In order to produce re-writable DNA-based digital storage that is randomly accessible, corresponding data may be assigned an address sequence. The address sequence may be selected from a set of address sequences. Further, the corresponding data may be encoded in a corresponding data sequence that does not conflict with the set of address sequences. As an example, an address sequence of length twenty may flank a corresponding data sequence (e.g., a corresponding data sequence of length 960) on a first side (e.g., the left side) of the corresponding data sequence and another address sequence of length twenty may flank a corresponding data sequence on a second side (e.g., the right side) of the corresponding data sequence.

The set of address sequences and corresponding data sequences may be designed using a two-step process. The first step may include designing address sequences of a given length that satisfy a set of constraints, making those address sequences suitable for selective random access. The first step may be semi-analytical, in that the first step may combine combinatorial methods with search techniques using a computing device. For example, the first step may select a set of possible address sequences based on combinatorics, and then perform a subsequent search of those possible address sequences to select a subset for use. In alternate embodiments, the first step may be purely analytical, in that the set of possible address sequences may be produced purely based on combinatorics.

The second step of designing address sequences and corresponding data sequences may involve encoding the information that is associated with the address sequences (i.e., address primers). The second step is described in a separate section of this description, while the first step is described below.

The set of constraints may avoid sequences that are prone to sequence errors. While the set of constraints might only be directly applied to address primer design, the set of constraints may also indirectly govern the information blocks (i.e., corresponding data sequences) associated with the address primers. In some embodiments, the following set of constraints may be imposed on the address sequences:

Constraint (1): The address sequences should have "constant GC content." If the sum of the number of guanines and cytosines within a DNA strand is equal, or nearly equal (e.g., within 1%, 5%, 10%, or 20% of 50%, or within 1-5 bases of 50%), to the sum of the number of adenines and thymines within the same DNA strand, that DNA stand has "constant GC content." DNA strands with 50% GC content are more stable than DNA strands with lower or higher GC content and have better coverage during sequencing. As described in a separate section, the corresponding data sequences may be encoded using prefix-synchronization. Thus, it may be beneficial to impose the "constant GC content" constraint on the address sequences (and their prefixes) so all fragments of encoded corresponding data sequences also have "constant GC content."

Figure 4A:
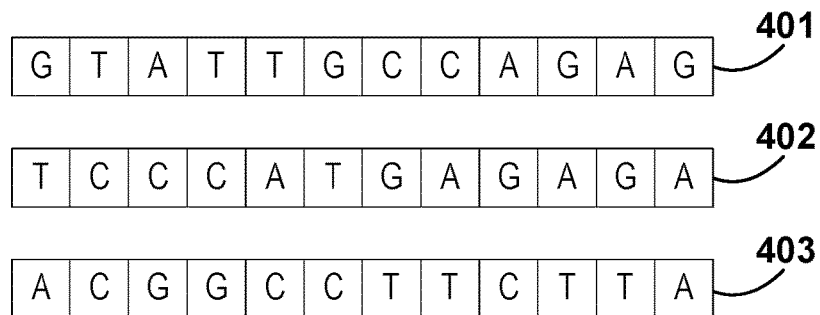
FIG. 4A illustrates a set of address primers that satisfy three constraints of address sequence design, according to example embodiments. Example address primer 401 corresponds to SEQ ID NO:01; Example address primer 402 corresponds to SEQ ID NO:02; and Example address primer 403 corresponds to SEQ ID NO:03.

Example address primers 401, 402, 403 illustrated in FIG. 4A exhibit the quality of having "constant GC content." The sum of the number of guanine and cytosine bases in the example address primers 401, 402, 403 (i.e., six guanines or cytosines) is equivalent to the sum of the number of thymine and adenine bases in the example address primers 401, 402, 403 (i.e., six thymines or adenines). Therefore, the example address primers 401, 402, 403 have "constant GC content." This quality is also exhibited in candidate address primers 421, 422, 423 that are illustrated in FIG. 4C. However, the candidate address primers 411, 412, 413 illustrated in FIG. 4B do not have "constant GC content." As such, the candidate address primers 411, 412, 413 might not be selected as address primers. In some embodiments, the amount of GC content that satisfies "constant GC content" may be lessened for long address primes or for address primers with an odd number of bases.

Constraint (2): The address sequences may also have a large mutual Hamming distance (the Hamming distance is a measure of the number of positions at which two sequences of equal length are different from one another, i.e., the number of positions at which their corresponding symbols disagree). By using address sequences that have a large mutual Hamming distance, the probability of erroneous address selection may be reduced. An example choice for a minimum Hamming distance may be equal to half of the length of the address sequence. For example, if the address primers are twenty bases in length, ten bases may be a sufficient threshold Hamming distance. In alternate embodiments, other measures of similarity between address strings may be used (e.g., the Levenshtein distance).

Example address primers 401, 402, 403 illustrated in FIG. 4A satisfy the above mutual Hamming distance constraint. As illustrated, the Hamming distance between address primer 401 and address primer 402 is twelve, the Hamming distance between address primer 401 and address primer 403 is twelve, and the Hamming distance between address primer 402 and address primer 403 is eleven (all greater than half the length of the address primers, which is six).

Figure 4B:
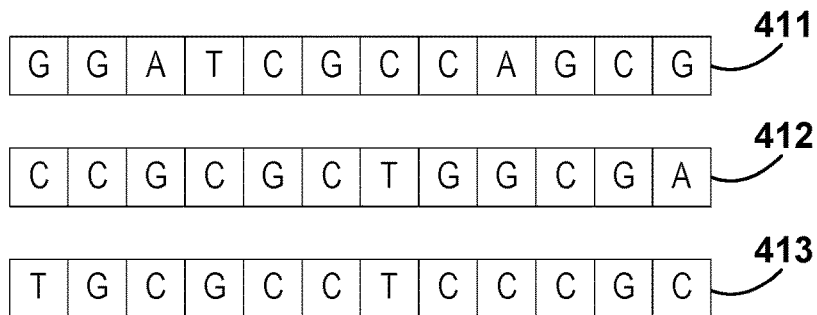
FIG. 4B illustrates a set of address primers that do not satisfy three constraints of address sequence design, according to example embodiments. Example address primer 411 corresponds to SEQ ID NO:04; Example address primer 412 corresponds to SEQ ID NO:05; and Example address primer 413 corresponds to SEQ ID NO:06.
Figure 4C:
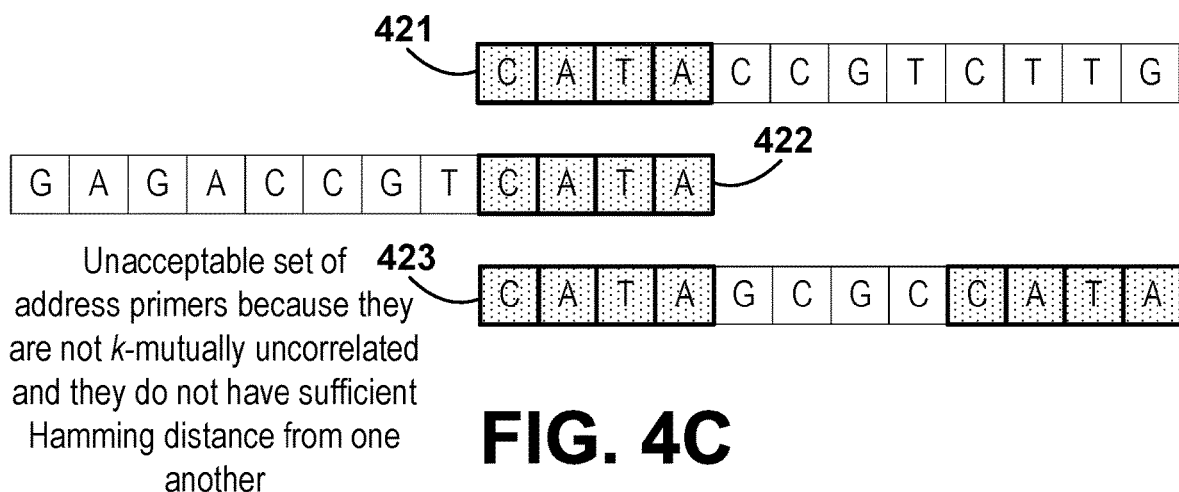
FIG. 4C illustrates a set of address primers that do not satisfy three constraints of address sequence design, according to example embodiments. Example address primer 421 corresponds to SEQ ID NO:07; Example address primer 422 corresponds to SEQ ID NO:08; and Example address primer 423 corresponds to SEQ ID NO:09.

Similarly, the candidate address primers 411, 412, 413 illustrated in FIG. 4B also exhibit sufficient mutual Hamming distance. As illustrated, the Hamming distance between candidate address primer 411 and candidate address primer 412 is twelve, the Hamming distance between candidate address primer 411 and candidate address primer 413 is nine, and the Hamming distance between candidate address primer 412 and candidate address primer 413 is eight (all greater than half the length of the address primers, which is six).

Conversely, the candidate address primers 421, 422, 423 illustrated in FIG. 4C do not exhibit sufficient mutual Hamming distance. As illustrated, the Hamming distance between candidate address primer 421 and candidate address primer 422 is four, the Hamming distance between candidate address primer 421 and candidate address primer 423 is four, and the Hamming distance between candidate address primer 422 and candidate address primer 423 is four (all less than half the length of the address primers, which is six). As such, the candidate address primers 421, 422, 423 might not be selected as address primers.

In some embodiments, bounded running digital sum (BRDS) codes may be used to satisfy constraint (1) and (2). The set of BRDS codes may then be modified or curated such that a subset of the BRDS codes satisfy constraint (3) described below.

Constraint (3): The set of address sequences may also be designed such that no address sequence has a prefix that appears as a suffix of the same or another address, and vice versa (i.e., the address sequences are "self-uncorrelated" and "mutually uncorrelated"). Because the address sequences may be used to provide unique identities for the corresponding data blocks (e.g., to permit random access), this constraint may ensure that their substrings do not appear in a "similar form" within other addresses. "Similarity", in this context, may refer to hybridization affinity, for example. In addition, this constraint may prevent long prefix-suffix matches from producing read assembly errors in blocks during concurrent information retrieval and sequencing.

In some embodiments, a minimum length of prefix may be defined, such that all prefixes equal to or longer than that length present within a set of address sequences do not appear as a suffix of the same or another address. Such a set of address sequences may be referred to as "weakly mutually uncorrelated." "Weakly mutually uncorrelated codes" differ from "mutually uncorrelated codes" in that "weakly mutually uncorrelated codes" allow short prefixes of codewords to also appear as suffixes of codewords. To more precisely describe a set of "weakly mutually uncorrelated" addresses, an integer, k, may be used. If $\mathcal{C} \subseteq \mathbb{F}_q^n$ and $1 \le k \le n$, $\mathcal{C}$ is a k-weakly mutually uncorrelated code if no proper prefix of length l, for all $l \ge k$, of a codeword in $\mathcal{C}$ appears as a suffix of any other codeword, including itself.

This relaxation of prefix-suffix constraints associated with "weakly mutually uncorrelated" addresses may improve code rates and allow for increased precision DNA fragment assembly and selective addressing. Further, "weakly mutually uncorrelated" addresses may allow for an encoding of any form of data (e.g., images), as opposed to only text or numerals.

As illustrated in FIG. 4A, the example set of address primers 401, 402, 403 do not have any prefixes that appear as suffixes in the same or other addresses. As such, the example set of address primers 401, 402, 403 satisfy the third constraint. Further, the example set of address primers 401, 402, 403 satisfy constraints (1)-(3), and thus could be selected as a set of three address primers to use as address sequences.

Similarly, as illustrated in FIG. 4B, the candidate set of address primers 411, 412, 413 do not have any prefixes that appear as suffixes in the same or other addresses. As such, the candidate set of address primers 411, 412, 413 satisfy the third constraint. However, since the candidate set of address primers 411, 412, 413 only satisfies constraint (2) and constraint (3), the candidate set of address primers 411, 412, 413 might not be selected as a set of three address primers to use as address sequences.

Conversely, as illustrated in FIG. 4C, the candidate set of address primers 421, 422, 423 do have prefixes of length four (CATA) which appear as suffixes in the same or other addresses and vice versa. As such, the candidate set of address primers 421, 422, 423 do not satisfy the third constraint. Because the candidate set of address primers 421, 422, 423 only satisfies constraint (1), the candidate set of address primers 421, 422, 423 may not be selected as a set of three address primers to use as address sequences.

Figure 4D:
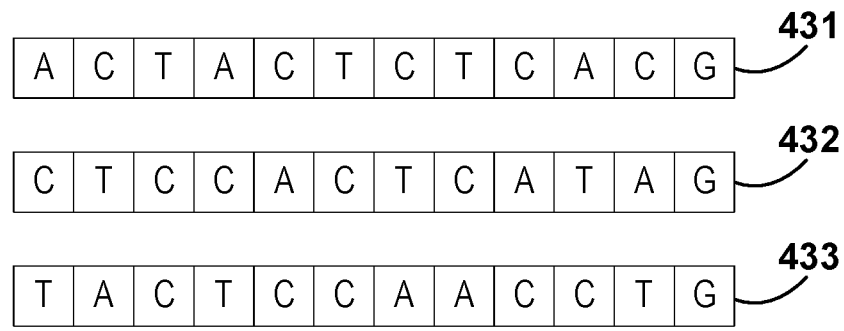
FIG. 4D illustrates a set of address primers that satisfy three constraints of address sequence design and also share a common concluding base, according to example embodiments. Example address primer 431 corresponds to SEQ ID NO:10; Example address primer 432 corresponds to SEQ ID NO:11; and Example address primer 433 corresponds to SEQ ID NO:12.

The example address sequences 401, 402, 403 illustrated in FIG. 4A are provided to illustrate a set of three address sequences that satisfy constraints (1), (2), and (3). In some embodiments, though, additional constraints may be imposed on the set of address sequences. For example, in some embodiments, the address sequences selected for use may all share a common base (e.g., guanine) as the last base in each sequence. Further, the address sequences selected for use may only use the three remaining bases (e.g., adenine, cytosine, and thymine), excluding the common base, to define the remainder of the address sequences. Such a set of example address sequences 431, 432, 433, which satisfy both constraints (1)-(3), as well as the common base constraint, is illustrated in FIG. 4D.

The set of address sequences should satisfy all three of the above constraints in order to be used. In some embodiments, additional constraints may be imposed, such as a lack of secondary folding characteristics for the corresponding DNA structures to avoid folding that would cause errors in PCR amplification and fragment rewriting. The lack of secondary structure at room temperature may be verified by the mfold and/or Vienna packages, for instance. An example of five address sequences that not only satisfy constraints (1)-(3), but also do not exhibit secondary folding characteristics is the following:

CGTAGTCAGCGTGTCAATCA (SEQ ID NO: 14)

TGCACAGTCGAGCTATCACA (SEQ ID NO: 15)

GACTGACTGATGACGACTGA (SEQ ID NO: 16)

-continued

GCTATATGCGAGTCGAGTCA (SEQ ID NO: 17)

GTACACTCAGCATCGACTCA (SEQ ID NO: 18)

In some embodiments, two address sequences may be selected to correspond to a single data sequence. For example, the data sequence may be appended on both sides with two separate, unique address sequences. Both of the address sequences may satisfy constraints (1)-(3). The address sequences on one end of the data sequences may be termed "start" address sequences, while the address sequences on the other end of the data sequences may be termed "end" address sequences. The use of two unique address sequences may enable rewritability of the data sequence from either end. For example, if the data to be rewritten is nearer to a "start" address sequence, a primer could be used to rewrite the data from the "start" end, and similarly for the "end" end.

The above construction of address sequences, including or not including the secondary folding constraint, may be analogous to a largest independent set problem. For example, the problem could be analogously defined as follows:

For a given length n and minimum Hamming distance d, let V denote the set of address sequences of length n that satisfy the following conditions:
Elements of V are GC-balanced
Elements of V avoid secondary structure
Construct a simple graph G(V, E), with vertices V and edges E, where (u, v)∈E, for u, v∈V, if one of the following conditions holds:
The Hamming distance between u and v is less than d
u and v are correlated, i.e., u and v share a proper prefix and suffix
Thus, it is verifiable that a set of strings A⊆V is an independent set in G if and only if A is a set address sequence that satisfies all four of the above conditions. Hence, the problem of finding the largest independent set in G may be equivalent to finding the largest set of address sequences of length n that satisfy the above conditions. Such a problem may be an NP-hard problem.

Constructing address sequences that simultaneously satisfy constraints (1) to (3) and determining bounds on the largest number of such sequences may take a significant amount of resources. Thus, a semi-constructive address designing process in which balanced error-correcting codes are designed independently, and subsequently expurgated so as to identify a large set of mutually uncorrelated sequences, may be used. This may be referred to as a "greedy approach for address construction." For example, the process may begin by selecting a single self-uncorrelated, GC-balanced DNA sequence (e.g., AATTACTAAGCGACCTTCTC; SEQ ID NO:19). Thereafter new address sequences may be added, one at a time, such that the total set of added sequences still satisfies constraints (1)-(3).

Each new address may be added by searching GC-balanced DNA sequences of the same length as the current set of address sequences (e.g., 20 bases) that have a minimum Hamming distance of at least half the length of the current set of addresses (e.g., 10). The first address sequence that is self-uncorrelated and mutually uncorrelated with the current address set may then be added to the address set. Secondary structure of the address sequences may also be taken into account in the "greedy approach for address construction," in some embodiments.

In alternate embodiments, a purely analytical method can be used to generate a complete set of address sequences. For given integers n and k≤n, let m=n−k+1 and let a, b, and c be the binary component words. The, $C \in \{A,T,C,G\}^n$ can be constructed according to the following steps:

(1) Encode a using a binary block code $C \subseteq \{0,1\}^{k-1}$ of length k−1, and minimum Hamming distance d. Let $\Phi_1$ denote the encoding function, so that $\Phi_1(a) \in C_1$.

(2) Generate a mutually uncorrelated code $C_2 \subseteq \{0,1\}^m$ of length m, dimension s, and minimum Hamming distance d. This may be done by fixing two positive integers, t and l, such that m=(l−1). For each codeword b ∈ $C_2$, b can be mapped to a word of length n=(t+1)l+1 given by:

$$a = 0^t 1 b_1^{l-1} 1 b_l^{2(l-1)} 1 \ldots b_{(t-1)(l-1)+1}^{t(l-1)} 1$$

Using the mutually uncorrelated code $C_2$, encode b. Let $\Phi_2$ denote the encoding function, so that $\Phi_2(b) \in C_2$.

(3) Generate a codeword c from a balanced code $C_3$ of length n, minimum Hamming distance d and of size $$A\left(n, d, \frac{n}{2}\right).$$

Let $\Phi_3$ denote the underlying encoding function, so that $\Phi_3(c) \in C_3$.

The output of the above encoder is $\Psi(\Phi_1(a), \Phi_2(b), \Phi_3(c))$, where $\Psi(a,b): \{0,1\}^s \times \{0,1\}^s \rightarrow \{A,T,C,G\}^s$ is an encoding function that maps the pair a, b to a DNA string $c=(c_1, \ldots, c_s) \in \{A,T,C,G\}^s$, according to the following rules:

$$\text{for } 1 \leq i \leq s, c_i \begin{cases} A & \text{if } (a_i, b_i) = (0, 0) \\ C & \text{if } (a_i, b_i) = (0, 1) \\ T & \text{if } (a_i, b_i) = (1, 0) \\ G & \text{if } (a_i, b_i) = (1, 1) \end{cases}$$

4. EXAMPLE DATA ENCODING

During a data storage process, once the address sequences are designed, various embodiments may include generating and selecting codeword blocks to encode the data to be stored. Codeword blocks may be sets of codewords that represent characters, strings, or sets of strings, for example. The codeword blocks may be selected to avoid replicating any of the address sequences, sufficiently long substrings of the address sequences, and substrings similar to the address sequences. This may be done to enable random access of the data by read processes described herein. For example, such a selection of codeword blocks may prevent DNA blocks that correspond to stored data from being accidentally accessed, amplified, or selected by a primer that is designed to access a specific address sequence (i.e., the primer may cut the DNA sequence nonspecifically at multiple regions if the address sequences were not independent from the codeword blocks, which could lead to reading errors or an inadvertent destruction of data).

One process of generating these codeword blocks may include generating a set of "comma free" and "prefix-synchronized" codes.

An example codeword block, $\mathcal{C}$, that includes a set of codewords of length N over an alphabet of size q is "comma free" if, and only if, for any pair of not necessarily distinct codewords $a_1 a_2 \ldots a_N$ and $b_1 b_2 \ldots b_N$ in $\mathcal{C}$, the N concatenations $a_2 a_3 \ldots a_N b_1, a_3 a_4 \ldots b_1 b_2, a_N a_1 \ldots b_{N-2} b_{N-1}$ are not in $\mathcal{C}$. "Comma free" codes may allow for an unambiguous determination of starting positions of codewords.

"Prefix-synchronized" codes have the property that every codeword in a set of "prefix-synchronized" codewords begin with a prefix $p = p_1 p_2 \ldots p_n$, which is followed by a constrained sequence $c_1 c_2 \ldots c_l$. In addition, each "prefix-synchronized" codeword in such a set of "prefix-synchronized" codewords has the property that, for any codeword $p_1 p_2 \ldots p_n c_1 c_2 \ldots c_l$ of length n+l, the prefix p does not appear as a substring of $p_2 \ldots p_n c_1 c_2 \ldots c_l p_1 p_2 \ldots p_{n-1}$. In other words, the constrained sequences $c_1 c_2 \ldots c_l$ of "prefix-synchronized" codes avoid the prefix p, which is used as an address.

Given the considerations described above for the address design (namely, that mutually uncorrelated addresses were chosen with a large Hamming distance), codewords that avoid one of the addresses in the set of address sequences may inherently avoid all other address sequences in the set of addresses.

An example methodology to produce such codewords is as follows. For a fixed set $\mathcal{A}$ of addresses sequences of length n, a set $\mathcal{C}_\mathcal{A}(l)$ is a set of sequences of length l such that each sequence in $\mathcal{C}_\mathcal{A}(l)$ does not contain any string belonging to $\mathcal{A}$. As such, when $l < n$, $\mathcal{C}_\mathcal{A}(l)$ is the set of sequences of length l. The following is an example process by which a set $\mathcal{J}$ of messages is encoded into $\mathcal{C}_\mathcal{A}(l)$.

To encode a $\mathcal{J}$ messages into $\mathcal{C}_\mathcal{A}(l)$, it may be assumed that $\mathcal{A}$ is mutually uncorrelated and that sequences in $\mathcal{A}$ end with the same base of DNA (e.g., G representing guanine). For example, only those candidate sequences that end in a common base of DNA may be selected to be a sequence in $\mathcal{A}$. An address $a = a_1 a_2 \ldots a_n \in \mathcal{A}$ may then be selected. Corresponding to address a, the following entities can be defined for $1 \leq i \leq n$:

$$\overline{A}_i = \{A, T, C\} \setminus \{a_i\}$$

$$a^{(i)} = a_1 \ldots a_i$$

In addition, the elements of $\overline{A}_i$ may be arranged in increasing order, alphabetically (i.e., A→C→T). Further, $\overline{a}_{i,j}$ may represent the $j^{th}$ smallest element in $\overline{A}_i$, for $1 \leq j \leq |\overline{A}_i|$, $|\overline{A}_i|$. For example, if $\overline{A}_i = \{C, T\}$, then $\overline{a}_{i,1} = C$ and $\overline{a}_{i,2} = T$.

A sequence of integers $S_{n,1}, S_{n,2}, \ldots$ that satisfies the following recursive formula is next defined:

$$S_{n,l} = \begin{cases} 3^l, & 1 \leq l < n \\ \sum_{i=1}^{n-1} |\overline{A}_i| S_{n,l-i}, & l \geq n \end{cases}$$

Further, the codeword design method may include, for an integer $l \geq 0$ and $y < 3^l$, letting $\theta_l(y) = \{A, T, C\}^l$ be a length-l ternary (i.e., base 3, but using DNA bases rather than numerals) representation of y. Correspondingly, $\theta^{-1}(W)$ may be defined such that, for each $W \in \{A, T, C\}^l$, $\theta^{-1}(W) = y$, wherein $\theta_l(y) = W$. Using such a framework, each integer between 0 and $S_{n,l} - 1$ may be mapped into a length-l sequence in $\mathcal{C}_\mathcal{A}(l)$, using the following $\text{ENCODE}_{a,l}$ function:

---

$X = \text{ENCODE}_{a,l}(x)$

BEGIN
1.     SET n = Length(a)
2.     IF (l ≥ n)
3.     {
4.       SET t = 1
5.       SET y = x
6.       WHILE (y ≥ $|\overline{A}_t| S_{n,l-t}$)
7.       {
8.         SET y = y − $|\overline{A}_t| S_{n,l-t}$
9.         SET t = t + 1
10.       }
11.       SET $c = \left\lfloor \dfrac{y}{S_{n,l-t}} \right\rfloor$
12.       SET d = y mod $S_{n,l-t}$
13.       RETURN $a^{(t-l)} \overline{a}_{t,c+1}$ $\text{ENCODE}_{a,l-t}(d)$
14.     }
15.     ELSE
16.     {
17.       RETURN $\theta_l(x)$
18.     }
19. END
END

---

In addition, the following $\text{DECODE}_a$ function may be used to convert a sequence of length l back to an integer between 0 and $S_{n,l} - 1$:

---

$x = \text{DECODE}_a(X)$

BEGIN
1.     SET n = Length(a)
2.     SET l = Length(X)
3.     ASSUME THAT X IS OF THE FORM $X = X_1 X_2 \ldots X_l$
4.     IF (l < n)
5.     {
6.       RETURN $\theta^{-1}(X)$
7.     }
8.     ELSE
9.     {
10.      FIND [u, v] SUCH THAT $a^{(u-1)} \overline{a}_{u,v} = X_1 \ldots X_u$
11.      RETURN $(\sum_{i=1}^{u-1} |\overline{A}_i| S_{n,l-i}) + (v-1) S_{n,l-u} + \text{DECODE}_a(X_{u+1} \ldots X_l)$
12.     }
13. END
END

---

The FIND function in the above $\text{DECODE}_a(X)$ method may be implemented in the following way:

---

$[u, v] = \text{FIND}(a, X, \overline{A}_1, \ldots, \overline{A}_n)$

BEGIN
1.     FOR (u = 1: Length(a))
2.     {
3.       FOR (v = 1: $|\overline{A}_u|$)
4.       {
5.         IF ($a^{(u-1)} \overline{a}_{u,v} = X_1 \ldots X_u$)
6.         {
7.           RETURN [u, v]
8.         }
9.         END
10.       }
11.       END
12.     }
13.     END
END

---

In the above FIND function, [u, v] is a set of two integers. Further, the outputs of the above FIND function may exist and may be unique.

To illustrate the results of the above encoding/decoding methods, an example is provided using the self-uncorrelated address string a=AGCTG. As described above, n corresponds to the length of the string, for address string a, n=5. For this example, a sequence of seven corresponding integers $S_{n,1}, S_{n,2}, \ldots, S_{n,7}$ may be defined, according to the above recursive formula. The resulting integers are:

$S_{n,1}=3$
$S_{n,2}=9$
$S_{n,3}=27$
$S_{n,4}=81$
$S_{n,5}=267$
$S_{n,6}=849$
$S_{n,7}=2715$

Below is an example mapping of x=550 to a corresponding 8-base sequence using corresponding to address string a:

```
                X = ENCODE_{a,8}(550)
BEGIN
1.      550 = 0 × S_{5,7} + 550
        ⇒ ENCODE_{a,8}(550) = CENCODE_{a,7}(550)

2.      550 = 0 × S_{5,6} + 550
        ⇒ ENCODE_{a,7}(550) = CENCODE_{a,6}(550)

3.      550 = 2 × S_{5,5} + 0 × S_{5,4} + 16
        ⇒ ENCODE_{a,6}(550) = AAENCODE_{a,4}(16)

4.      16 = 0 × 3³ + 1 × 3² + 2 × 3¹ + 1 × 3⁰
        ⇒ ENCODE_{a,4}(16) = ATCT
        ⇒ ENCODE_{a,8}(550) = CCAAATCT
END
```

As shown, the algorithm involves four iterations. Further, $\overline{A}_1=\{C,T\}$, $\overline{A}_2=\{A,C,T\}$, $\overline{A}_3=\{A,T\}$, $\overline{A}_4=\{A,C\}$, and $\overline{A}_5=\{A,C,T\}$. Additionally, $\overline{a}_{1,1}=C$, $\overline{a}_{1,2}=T$, $\overline{a}_{2,1}=A$, $\overline{a}_{2,2}=C$, $\overline{a}_{2,3}=T$, $\overline{a}_{3,1}=A$, $\overline{a}_{3,2}=T$, $\overline{a}_{4,1}=A$, $\overline{a}_{4,2}=C$, $\overline{a}_{5,1}=A$, $\overline{a}_{5,2}=C$, and $\overline{a}_{5,3}=T$.

In the first iteration, n=5, l=8, t=1, and y=550. The product $|\overline{A}_1|S_{5,7}$ is 2×2715=5430. This results in the while loop being skipped. Therefore, c=0 and d=550. Since $a^{(0)}$ is the empty string and $\overline{a}_{1,1}=C$, the base derived from this iteration is cytosine.

In the second iteration, n=5, l=7, t=1, and y=550. The product $|\overline{A}_2|S_{5,6}$ is 3×849=2547. This results in the while loop being skipped. Therefore, c=0 and d=550. Since $a^{(0)}$ is the empty string and $\overline{a}_{1,1}=C$, the base derived from this iteration is cytosine.

In the third iteration, n=5, l=6, t=1, and y=550. The product $|\overline{A}_3|S_{5,5}$ is 2×267=534. This results in the while loop being applied until t=2 and y=16. Therefore, c=0 and d=16. Since $a^{(1)}=A$ and $\overline{a}_{2,1}=A$, the bases derived from this iteration are adenine and adenine.

In the third iteration, n=5, l=4, t=1, and y=16. The else branch of the if statement is triggered, and $\theta_4(16)$ is returned. The evaluation of $\theta_4(16)$ involves applying a ternary coding over $\{A,T,C\}^4$ where A=0, T=1, and C=2, resulting in the string ATCT, or adenine, thymine, cytosine, and thymine. Accordingly, the final string of bases is CCAAATCT.

Below is an example retrieval of the corresponding integer, x, from the sequence

X = CCAAATCT.

```
                x = DECODE_a(X)
BEGIN
1.      ⇒ DECODE_a(CCAAATCT) = 0 × S_{5,7} +
          DECODE_a(CCAAATCT)

2.      ⇒ DECODE_a(CAAATCT) = 0 × S_{5,6} + DECODE_a(AAATCT)

3.      ⇒ DECODE_a(AAATCT) = 2 × S_{5,5} + 0 × S_{5,4} +
          DECODE_a(ATCT)

4.      ⇒ DECODE_a(ATCT) = 16
        ⇒ DECODE_a(CCAAATCT) = 2 × S_{5,5} + 16 = 550
END
```

As shown, this algorithm also involves four iterations. As was the case for the ENCODE algorithm, $\overline{A}_1=\{C,T\}$, $\overline{A}_2=\{A,C,T\}$, $\overline{A}_3=\{A,T\}$, $\overline{A}_4=\{A,C\}$, and $\overline{A}_5=\{A,C,T\}$. Moreover, $\overline{a}_{1,1}=C$, $\overline{a}_{1,2}=T$, $\overline{a}_{2,1}=A$, $\overline{a}_{2,2}=C$, $\overline{a}_{2,3}=T$, $\overline{a}_{3,1}=A$, $\overline{a}_{3,2}=T$, $\overline{a}_{4,1}=A$, $\overline{a}_{4,2}=C$, $\overline{a}_{5,1}=A$, $\overline{a}_{5,2}=C$, and $\overline{a}_{5,3}=T$.

In the first iteration, n=5 and l=8. The FIND function results in u=1 and v=1. The term $\Sigma_{i=1}^{u-1}|\overline{A}_i|S_{5,8-i}$ is 0, and the term $(v-1)S_{5,7}$ also is 0. The next iteration of DECODE is applied to the string CAAATCT.

In the second iteration, n=5 and l=7. The FIND function results in u=1 and v=1. The term $\Sigma_{i=1}^{u-1}|\overline{A}_i|S_{5,7-i}$ is 0, and the term $(v-1)S_{5,6}$ also is 0. The next iteration of DECODE is applied to the string AAATCT.

In the third iteration, n=5 and l=6. The FIND function results in u=2 and v=1. The term $\Sigma_{i=1}^{u-1}|\overline{A}_i|S_{5,6-i}$ is 2×267=534, and the term $(v-1)S_{5,5}$ is 0. The next iteration of DECODE is applied to the string ATCT.

In the third iteration, n=5 and l=4. The main branch of the if statement is triggered, and $\theta^{-1}(ATCT)$ is returned. The evaluation of $\theta^{-1}(ATCT)$ involves reversing the ternary coding over $\{A,T,C\}^4$ where A=0, T=1, and C=2. Since $0\times3^3+1\times3^2+2\times3^1+1\times3^0$, the resulting value is 0+9+6+1=16. Finalizing the recursion, the value returned by DECODE is 534+16=550.

Note that the above encoding/decoding methods are provided as examples, and are not to be viewed as limiting. In other embodiments, for example, address sequences of various lengths, codewords of various lengths, and/or different bases at the end of the codewords (e.g., thymine or adenine instead of guanine) may be used.

In some embodiments, the encoding method may further include a controlled "perturbing" of long prefixes in the encoded information. This may prevent cross hybridization between address primers used for selection and addresses encoding the data. For example, one way of "perturbing" long prefixes includes selecting those prefixes that are of a length greater than a predefined threshold length and swapping second quarter and the third quarter (i.e., the central portions) of the bases, thereby cyclically shifting the bases by half the prefixes length. Using the example address a=AGTAAGTCTCGCAGTCATCG (SEQ ID NO:20), if the prefix $a^{(16)}$=AGTAAGTCTCGCAGTC (SEQ ID NO:21) appears as a subword V in X=ENCODE$_{a,l}$(x), then X can be modified to X' by mapping V to V'=AGTAATCGGTCCAGTC (SEQ ID NO:22). The shifting process of X is illustrated below:

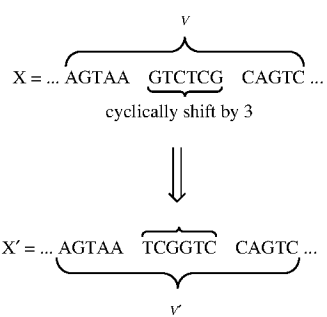

In addition, the "prefix-synchronized" coding described may support error-detection and limited error-correction. The error-correction is achieved by determining if each substring of the sequence represents a prefix or shifted prefix of the given address sequence and, if the substring does not represent a prefix or shifted prefix, making modifications to the sub string.

5. EXAMPLE RANDOM ACCESS WRITING

The example embodiment of FIG. 5A illustrates multiple data blocks 510, 520, 530 within a set of data blocks. The data blocks 510, 520, 530 may each include address sequences 511, 521, 531 of length twenty base pairs flanking corresponding data sequences 512, 522, 532 (e.g., corresponding data sequences of length 960 base pairs) on a first side (e.g., the left side) of the corresponding data sequences 512, 522, 532 and other address sequences 513, 523, 533 of length twenty base pairs flanking the corresponding data sequences 512, 522, 532 on a second side (e.g., the right side) of the corresponding data sequences 512, 522, 532. As illustrated by different patterns in FIG. 5A, the address sequences on either side of the data blocks (e.g. address sequence 511 and 513) represent unique, different addresses. The address sequences 511, 513, 521, 523, 531, 533 on both sides of the corresponding data sequences 512, 522, 532 may provide specificity of access. The corresponding data sequences 512, 522, 532 may be made up of individual data sub-blocks 551-562 that are each twenty base pairs in length, for example.

As illustrated in the example embodiment of FIG. 5A, the data blocks 510, 520, 530 may be 1,000 base pairs in length. In alternate embodiments, other lengths of data blocks, address sequences, corresponding data sequences, and/or number of corresponding data sequences may be used. Address sequences shorter than 1,000 base pairs, for example, may be less expensive to synthesize, but may also incur an increased storage overhead. The inverse may be true for address sequences longer than 1,000 base pairs.

Figure 5B:
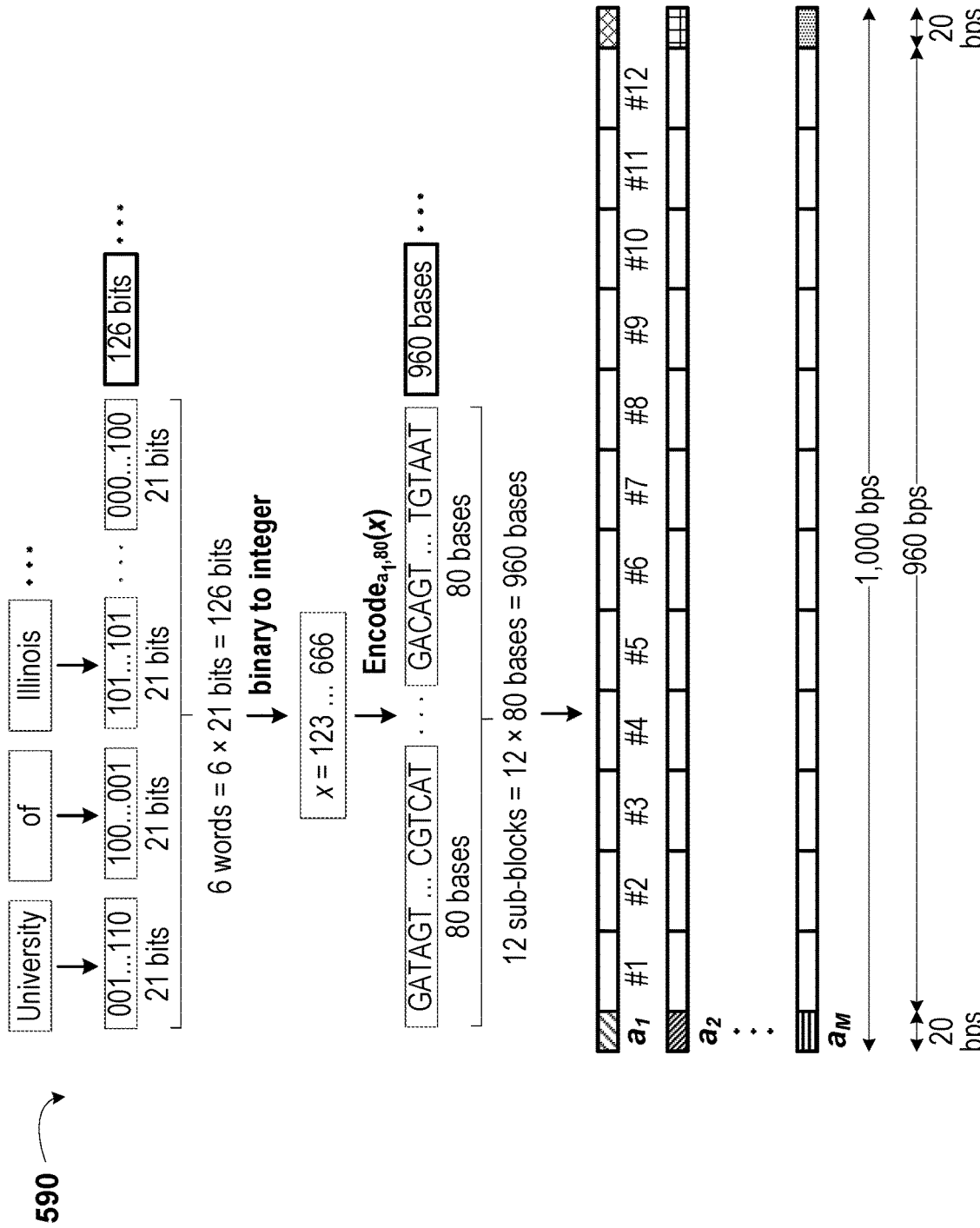
FIG. 5B illustrates an encoding scheme, according to example embodiments.

An example encoding/writing process is presented that encodes a set of textual data (e.g., from a text file or a scanned image file) into the corresponding data sequences 512, 522, 532. The example process presented may include a specialized compaction scheme suitable for rewritability of the corresponding data sequences 512, 522, 532. The example process 590 is illustrated in FIG. 5B.

The example process 590 may include counting different words in the textual data and tabulating them in a dictionary. Each word in the dictionary may then be converted into a binary sequence of a length, $s$, that is sufficient to allow for an encoding of the entire dictionary. Each set of six consecutive words, for example, within the textual data are subsequently grouped into extended binary sequences (e.g., of length $6 \times s$). The number of jointly encoded words grouped into the extended binary sequences may be selected to make rewrites straightforward and to avoid error propagation due to variable code lengths.

After organizing the set of consecutive words into extended binary sequences, the extended binary sequences are then translated into DNA blocks, of length d for example, using the DNA "prefix-synchronized" codes described above. These DNA blocks may consequently be synthesized, in some embodiments. In the embodiment illustrated in FIG. 5A, the length d is eighty base pairs for each data sub-block 551-562.

As an example, the process described above could be used to encode two files of size 17 KB that contain the introductory sections of Wikipedia pages of six universities (e.g., Berkeley, Harvard, MIT, Princeton, Stanford, and University of Illinois Urbana-Champaign). In such a file, there may be 1,933 words in the text, 842 of which being distinct (words may be defined as elements of the text separated by a space). If a set of data blocks of length 1000 bps, having two address sequences at each end of length 20 bps (thus leaving a data sequence of 960 bps), were used to represent this data, the 1,933 words may then be mapped to $$\left\lceil \frac{1933}{72} \right\rceil = 27 \text{ DNA blocks}$$

of length 1,000 bps by grouping six words into fragments, and combining 12 fragments for prefix-synchronized encoding.

By comparison, American Standard Code for Information Interchange (ASCII) encoding, without compression, may use 90,118 bits (12,874 characters, each of bit-length 7) to represent the data. If a set of data blocks of length 1000 bps, having two address sequences at each end of length 20 bps (thus leaving a data sequence of 960 bps), were used to represent this ASCII data, $$\left\lceil \frac{90118}{2 \times 960} \right\rceil = 47 \text{ DNA blocks}$$

DNA blocks may be allocated. As demonstrated the first method, which uses 27 DNA blocks, may offer an almost 1.7-fold improvement in description length compared to the uncompressed ASCII encoding scheme.

Further, the data within each data sub-block 551-562 may be selectively accessed and rewritten. The selective access may include using a primer corresponding to a unique address to make a selective query of the appropriate data block from a mixture of multiple data blocks and amplifying the appropriate data block (e.g., using polymerase chain reaction, PCR).

One example method of content "rewriting" may include synthesizing new address sequences with unique primers. This may be more efficient for than rewriting information using the current set of address sequences, especially if the region to be rewritten has a length of several hundreds of base pairs or more.

A second example method of content rewriting may include generating changes of the amplified data block using DNA editing. This example method may be superior to synthesizing new address sequences when modifying relatively short substrings of the encoded data block.

Figure 6A:
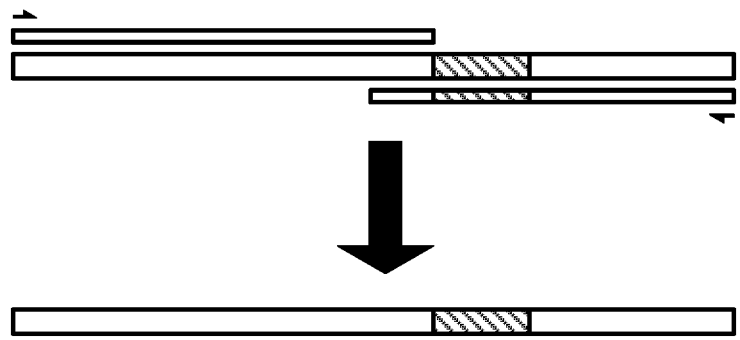
FIG. 6A illustrates a method of rewriting a data sequence, according to example embodiments.

The second method may be performed using a variety of DNA editing techniques. For example, the GBLOCKS® method illustrated in FIG. 6A could be used to edit the DNA. In the GBLOCKS® method illustrated in FIG. 6A, GBLOCKS® are chemically synthesized, double-stranded genomic fragments used as primers or for genome editing. In an example embodiment, the GBLOCKS® may be designed with complementary base pair overlaps (e.g., 30 bp in length) on the 3' strand that overlap with the address sequence portion of the data sequence to be rewritten. Using such a GBLOCKS® design, a mesophilic 5' exonuclease may cleave the data block from the 5' end before being inactivated. This may generate complementary 3' overhangs, which may subsequently be annealed. In some embodiments, a DNA polymerase may fill in any gaps in the data sequence. Further, a thermophilic DNA ligase may then join DNA segments (e.g., the address sequence segment to the data sequence segment).

Figure 6B:
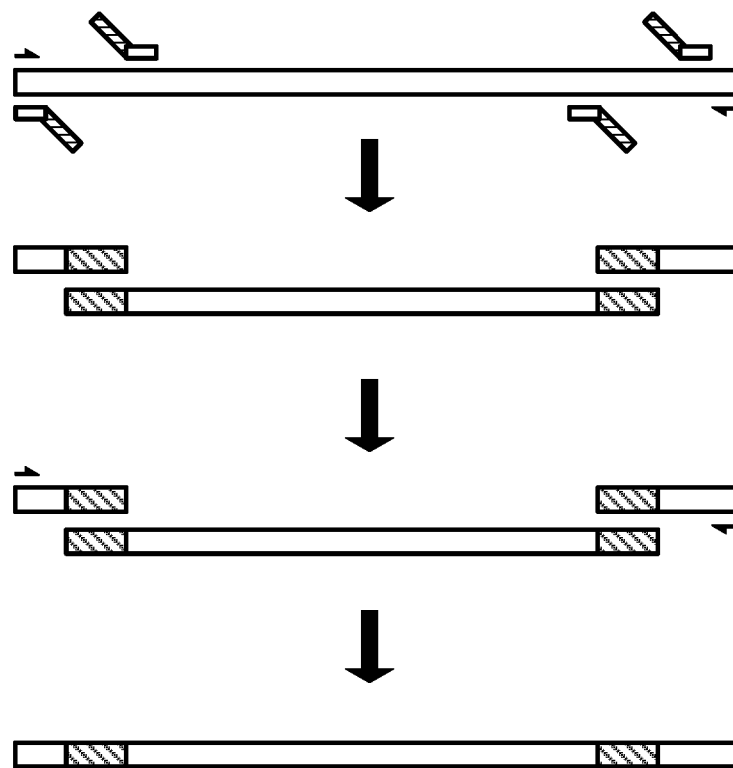
FIG. 6B illustrates a method of rewriting a data sequence, according to example embodiments.

As another example, the overlap extension polymerase chain reaction (OE-PCR) method illustrated in FIG. 6B could alternatively be used. In OE-PCR, rewriting may be done in several steps using short, relatively inexpensive primers. Comparatively, the GBLOCKS® method may include synthesizing longer, and comparatively more expensive, primers. In the OE-PCR method illustrated in FIG. 6B, point editing/mutations or splicing may be used. For example, in some embodiments, two address primers corresponding with the address sequences at each end of the data block may be used. Each segment of DNA may then be prepared such that it has a 5' overhang that is complementary to the data block to be rewritten. The DNA sequences may then be annealed and replicated. During replication, the address sequence may be extended by a new data sequence that is complementary to the data sequence to which the address sequence is to be joined. Further, the address primer on the splicing DNA may be extended by the data sequence which is to be spliced onto the address sequence. The two segments of DNA (i.e., the splicing DNA and the DNA to be rewritten) may then be mixed and PCR may be carried out using only primers for the ends opposite the ends which will overlap during the rewriting. Thereafter, the overlapping complementary sequences may serve as primers and the two sequences may fuse.

Once a content rewriting method has been performed, gel electrophoresis combined with Sanger sequencing may be performed on a sample to test whether the rewriting processes worked correctly.

6. EXAMPLE RANDOM ACCESS READING

Figure 7:
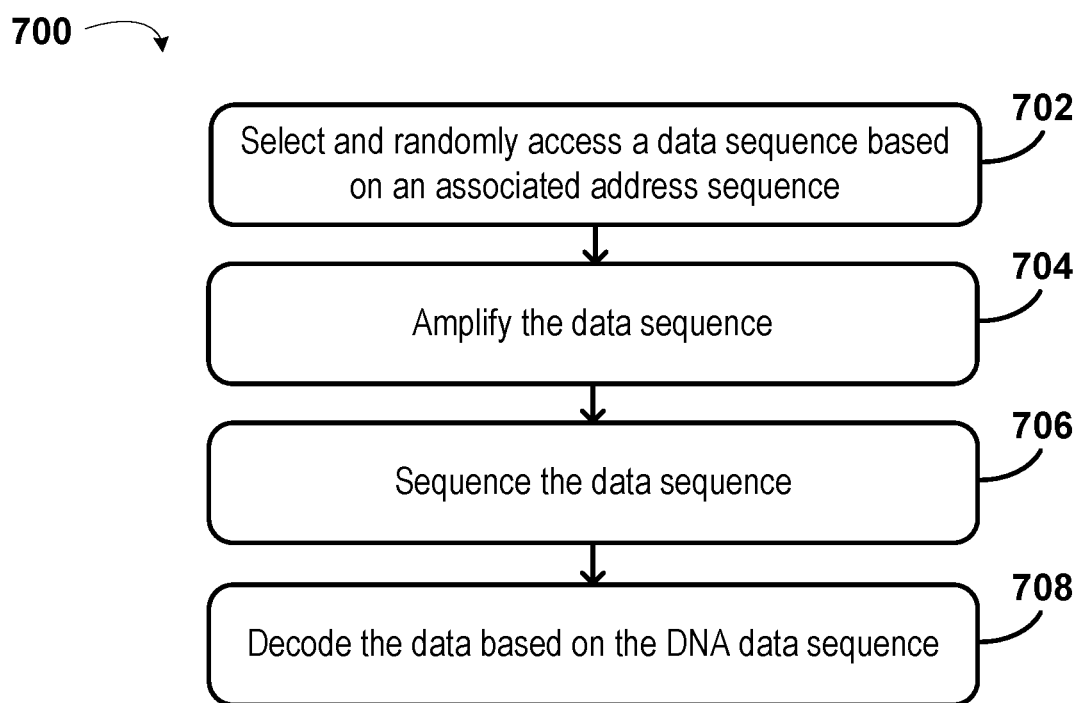
FIG. 7 illustrates a method of reading a data sequence, according to example embodiments.

Once encoded/written, the data sequences may later be read for data retrieval. As described above, the data sequences, based on their associated address sequences, may be randomly accessed for reading. An example method 700 of performing the random access reading is illustrated in FIG. 7.

At block 702, the method 700 may include selecting the specific data sequence, based on its associated address sequence, from the "soup" of DNA that contains all the address sequences and corresponding data sequences (here, a DNA "soup" refers to an unordered mixture of DNA). Because the associated address sequence is unique among other address sequences and subsections of other data sequences within the "soup", due to the way in which it was generated, such a selection of the address sequence is also unique. The selection may be made using a primer which cuts a strand of DNA in the soup at the location of the address sequence. Even given a relatively extremely low likelihood of error in selecting the correct address sequence (e.g., between 1 in $10^{15}$ or 1 in $10^{16}$), the selection (i.e., block 702) may be performed multiple times (e.g., three times). The selection may be performed multiple times so that in later blocks a majority rule can be applied, which may serve as a way of eliminating potential mistaken readings through repetition (i.e., multiple data sequences may be compared against one another for consistency). Block 702 may include selecting one or more address sequences and an associated data sequence, together comprising a data block.

At block 704, the data sequence, or a data block which includes both the relevant address sequence(s) and the corresponding data sequence, may be amplified. Block 704 may be performed using PCR, for example. PCR may amplify the address sequence(s) and the corresponding data sequence at a rapid rate (e.g., between $2^{30}$ and $2^{40}$ times amplification per hour). Similarly, if multiple selections were made (e.g., if three address sequence selections were made in block 702), block 704 may be repeated multiple times, one for each data sequence.

At block 706, the method 700 may include DNA sequencing the data sequence. This may include Sanger sequencing the data sequence, for example. As with prior blocks, if multiple selections and amplifications were made (e.g., if three address sequence selections were made in block 702 and three data sequence amplifications were made in block 704), block 706 may be repeated multiple times, one for each data sequence.

At block 708, the method 700 may include decoding the data based on the DNA data sequence. Decoding the data may include taking a list of the bases sequenced at block 706, and converting it to numerals or text based on the above described decoding scheme. Further, such a decoding may be performed by a computing device, for example. As with prior blocks, if multiple selections, amplifications, and DNA sequencings were performed (e.g., if three address sequence selections were made in block 702, three data sequence amplifications were made in block 704, and three DNA sequencings were performed in block 706), block 708 may be repeated multiple times, one for each DNA sequence.

In some embodiments, if multiple data sequences were selected, amplified, and sequenced, the method 700 of randomly accessing the data may additionally include comparing the results from multiple DNA sequences to each other. After a comparison, a "correct" sequence may be selected based on majority rule. For example, if three DNA sequences were produced from three different amplified, selected data sequences, whichever candidate DNA sequence is represented in at least two of the three compared DNA sequences may be determined the "correct" sequence that contains the requested data. The majority rule comparison may be performed on a base by base basis, for example. Such a comparison and selection based on majority rule may additionally or alternatively be applied at the stage of the decoded data rather than at the stage of the DNA sequences. Further, if each of the three DNA sequences are unique (i.e., all three are dissimilar), the blocks of method 700 may be repeated to yield a clear majority winner. This repetition may serve as an additional way of eliminating mistaken readings.

During the reading process, the data sequence being read may be selected from the "soup" and analyzed. In doing so, that respective data sequence may be removed from the "soup" and/or destroyed. As such, the reading process may include a replenishment of the read data sequence. The replenishment may include return a copy of the amplified/DNA sequenced data sequence to the "soup."

7. EXAMPLE OPERATIONS

Figure 8:
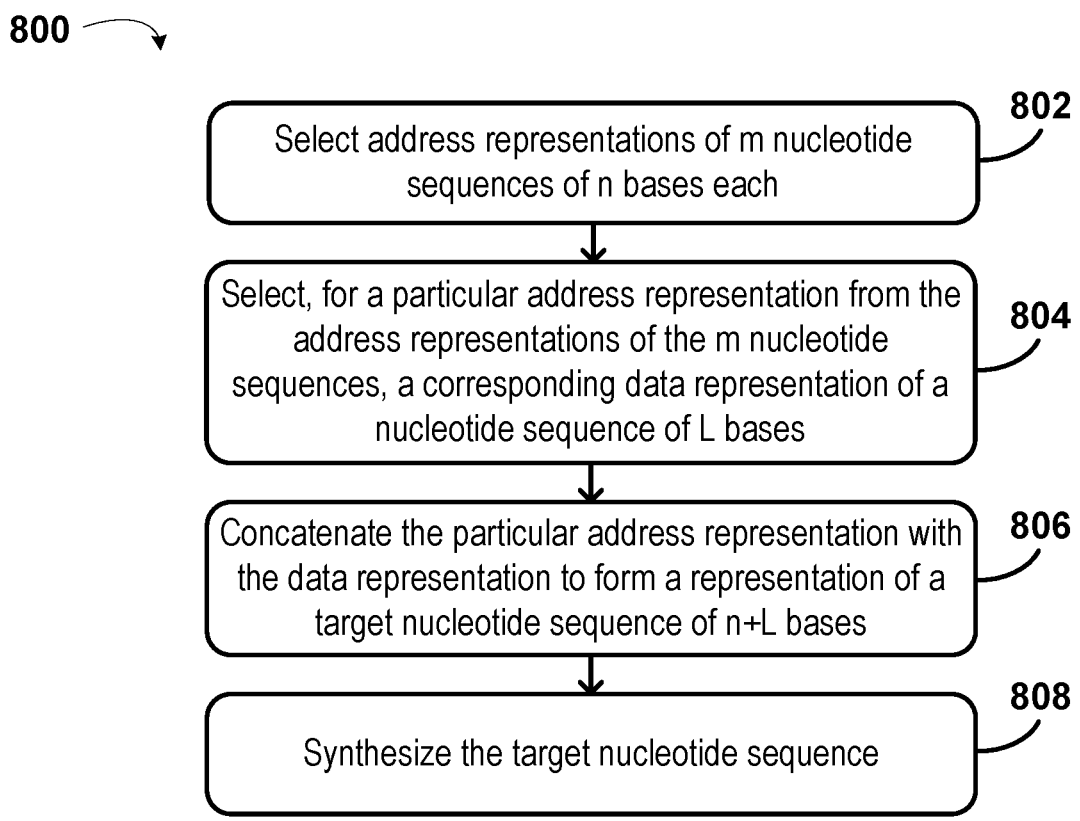
FIG. 8 depicts a flow chart illustrating a method, according to example embodiments.

FIG. 8 is a flow chart illustrating an example embodiment of a method 800. The method 800 illustrated by FIG. 8 may be carried out by a computing device, such as computing device 200, and/or a cluster of computing devices, such as server cluster 304. However, the method 800 can be carried out by other types of devices or device subsystems. For example, the method 800 could be carried out by a portable computer, such as a laptop or a tablet device.

At block 802, the method 800 may include selecting address representations of m nucleotide sequences of n bases each. Each of the address representations of m nucleotide sequences may consist of approximately 50% guanine and cytosine content. In some embodiments, consisting of approximate 50% guanine and cytosine content may include each of the address representations of m nucleotide sequences being 0 to 3 bases away from 50% guanine and cytosine content. Each of the address representations may also be self-uncorrelated. The address representations may also be mutually uncorrelated with one another. Further, all of the address representations may end with a particular base (e.g., guanine). In some embodiments, the address representations might also not contain folding structures.

In some embodiments, selecting the address representations may include performing an iterative greedy search over a space of potential address representations of nucleotide sequences of n bases each until a set of the address representations of m nucleotide sequences are found. The search may include selecting a potential address representation from the space of potential address representations, the potential address representation comprising approximately 50% guanine and cytosine content and having a Hamming distance of at least n/2 from all other address representations in the set of the address representations. The search may also include determining that the potential address representation is self-uncorrelated, mutually uncorrelated with all address representations in the set of the address representations, and does not include secondary structure. Further, the search may include placing the potential address representation in the set of the address representations.

Additionally or alternatively, selecting the address representations may include mapping address representation selection to a largest independent set problem. Selecting the address representations may also include using an approximation algorithm to approximate a solution to the largest independent set problem. Further, selecting the address representations may include mapping (i) the solution to the largest independent set problem to (ii) the address representations.

In some embodiments, the n sets of bases exclude the particular base and the respectively associated bases of the particular address representation. Additionally or alternatively, in some embodiments, the n bases of the particular address representation may be ordered such that no proper prefix of length j, for all j greater than or equal to k and less than n, is a suffix of any of the address representations of m nucleotide sequences. Further, in such embodiments, the n bases of the particular address representation may be ordered such that no proper prefix is a suffix of any of the address representations of m nucleotide sequences.

At block 804, the method 800 may include selecting, for a particular address representation from the address representations of the m nucleotide sequences, a corresponding data representation of a nucleotide sequence of L bases. The data representation encodes an integer value less than $3^L$ that is a sum of a first addend and a second addend. The data representation includes a first subsequence of bases encoding the first addend followed by a second subsequence of bases encoding the second addend. The first addend is encoded based on mappings of subvalues of the first addend to n sets of bases respectively associated with the n bases of the particular address representation. The second subsequence of bases is a ternary encoding of the second addend over a set of three bases not including the particular base. The data representation is uncorrelated with each of the address representations. The ternary encoding may represent each of digits 0, 1, and 2, with respective different bases of the set of three bases.

In some embodiments, L may be less than n. Further, in such embodiments, the first subsequence of bases may be zero length, and the second subsequence of bases may be L length.

At block 806, the method 800 may include concatenating the particular address representation with the data representation to form a representation of a target nucleotide sequence of n+L bases.

At block 808, the method 800 may include synthesizing the target nucleotide sequence. Synthesizing the target nucleotide sequence may include assembling pools of oligonucleotide building blocks into increasingly larger DNA. Such an assembly may be performed using chemical oligonucleotide synthesis (e.g., H-phosphonate, phosphodiester, phosphotriester, or phosphite triester/phosphoramidite) or oligo synthesis platforms (e.g., column-based oligo synthesis, array-based oligo synthesis, or complex strand and gene synthesis). For example, column-based oligo synthesis may include stepwise addition of nucleotides to an immobilized chain of nucleotides on a solid support, where the immobilized chain grows each time an additional nucleotide is added. Each addition may include (i) de-blocking, (ii) coupling or condensation, (iii) capping, and (iv) oxidation. Alternatively, the array-based oligo synthesis may include photolithography or ink-jet base printing of picoliters of nucleotides. In other embodiments, approaches that include ligation of phosphorylated overlapping oligonucleotides in high stringency conditions may be used for synthesis. Further, synthesizing the target nucleotide sequence may include performing error correction.

In some embodiments, the method 800 may also include, before synthesizing the target nucleotide sequence, concatenating a further particular address representation of the address representations to an end of the data representation to form a target nucleotide sequence of 2n+L bases. The data representation is disposed between the particular address representation and the further particular address representation.

Figure 9:
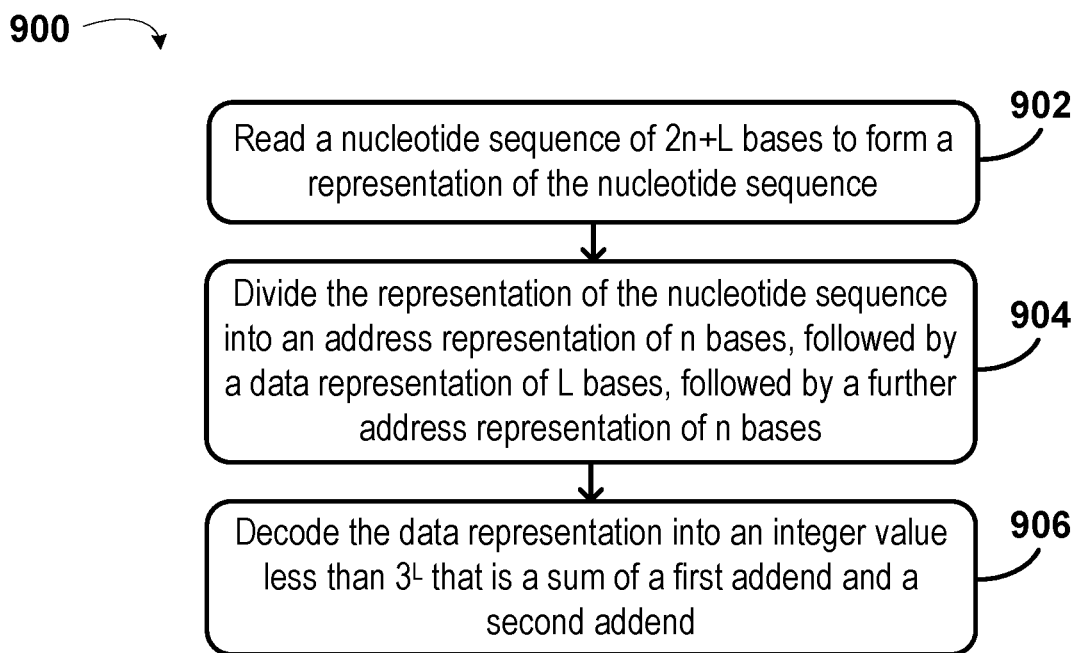
FIG. 9 depicts a flow chart illustrating a method, according to example embodiments.

FIG. 9 is a flow chart illustrating an example embodiment of a method 900. Some aspects of the method 900 illustrated by FIG. 9 may be carried out by a computing device, such as computing device 200, and/or a cluster of computing devices, such as server cluster 304. However, the method 900 can be carried out by other types of devices or device subsystems. For example, the method 900 could be carried out by a portable computer, such as a laptop or a tablet device.

At block 902, the method 900 may include reading a nucleotide sequence of 2n+L bases to form a representation of the nucleotide sequence. In some embodiments, the representation of the nucleotide sequence might not contain folding structures. Further, the representation of the nucleotide sequence may consist of approximately 50% guanine and cytosine content (e.g., within 1%, 5%, 10%, or 20% of 50% guanine and cytosine content, by number of bases). In such embodiments, the representation of the nucleotide sequence may be between 0 and 3 bases away from 50% guanine and cytosine content.

At block 904, the method 900 may include dividing the representation of the nucleotide sequence into an address representation of n bases, followed by a data representation of L bases, followed by a further address representation of n bases. The address representation and the further address representation are each uncorrelated with one another, self-uncorrelated, and end with a particular base (e.g., guanine).

At block 906, the method 900 may include decoding the data representation into an integer value less than $3^L$ that is a sum of a first addend and a second addend. The data representation includes a first subsequence of bases encoding the first addend followed by a second subsequence of bases encoding the second addend. The first addend is encoded based on mappings of subvalues of the first addend to n sets of bases respectively associated with the n bases of the address representation. The second subsequence of bases is a ternary encoding of the second addend over a set of three bases not including the particular base (e.g., the ternary encoding may represent each of digits 0, 1, and 2 with respective different bases of the set of three bases). The data representation is uncorrelated with each of the address representations.

In some embodiments, the n sets of bases may exclude the particular base and the respectively associated bases of the address representation. Additionally or alternatively, in some embodiments, n may be less than L, the first subsequence of bases may be zero length, and the second subsequence of bases may be L length. In still other embodiments, the n bases of the address representation may be ordered such that no proper prefix of length j, for all j greater than or equal to k and less than n, is a suffix of the further address representation.

Figure 10:
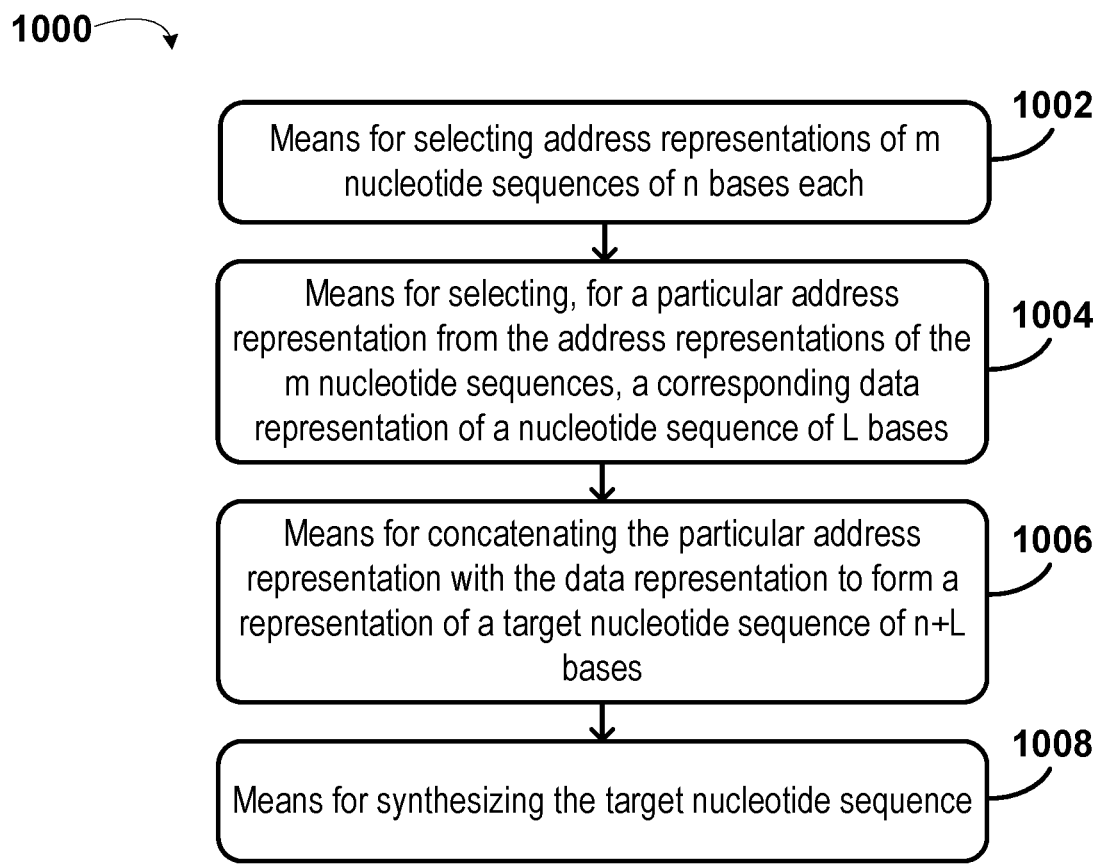
FIG. 10 depicts a flow chart illustrating a method, according to example embodiments.

FIG. 10 is a flow chart illustrating an example embodiment of a method 1000. Some aspects of the method 1000 illustrated by FIG. 10 may be carried out by a computing device, such as computing device 200, and/or a cluster of computing devices, such as server cluster 304. However, the method 1000 can be carried out by other types of devices or device subsystems. For example, the method 1000 could be carried out by a portable computer, such as a laptop or a tablet device.

At block 1002, the method 1000 may include a means for selecting address representations of m nucleotide sequences of n bases each. Each of the address representations of m nucleotide sequences may consist of approximately 50% guanine and cytosine content. Each of the address representations may also be self-uncorrelated. The address representations are mutually uncorrelated with one another. All of the address representations end with a particular base (e.g., guanine).

At block 1004, the method 1000 may include a means for selecting, for a particular address representation from the address representations of the m nucleotide sequences, a corresponding data representation of a nucleotide sequence of L bases. The data representation encodes an integer value less than $3^L$ that is a sum of a first addend and a second addend. The data representation includes a first subsequence of bases encoding the first addend followed by a second subsequence of bases encoding the second addend. The first addend is encoded based on mappings of subvalues of the first addend to n sets of bases respectively associated with the n bases of the particular address representation. The second subsequence of bases is a ternary encoding of the second addend over a set of three bases not including the particular base. The data representation is uncorrelated with each of the address representations.

At block 1006, the method 1000 may include a means for concatenating the particular address representation with the data representation to form a representation of a target nucleotide sequence of n+L bases.

At block 1008, the method 1000 may include a means for synthesizing the target nucleotide sequence. Such synthesis may occur according to the techniques described above.

The embodiments of FIGS. 8-10 may be simplified by the removal of any one or more of the features shown therein. Further, these embodiments may be combined with features, aspects, and/or implementations of any of the previous figures or otherwise described herein.

8. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed is:

1. A method comprising:

reading, by way of random access, a physical nucleotide sequence of 2n+L bases to form a digital representation of the physical nucleotide sequence, wherein the reading involves amplifying the physical nucleotide sequence and sequencing the physical nucleotide sequence;

dividing the digital representation of the physical nucleotide sequence into an address representation of n bases, followed by a data representation of L bases, followed by a further address representation of n bases, wherein the address representation and the further address representation each are uncorrelated with one another, self-uncorrelated, and end with a particular base;

decoding the data representation into an integer value less than 3L that is a sum of a first addend and a second addend, wherein the data representation includes a first subsequence of bases encoding the first addend followed by a second subsequence of bases encoding the second addend, wherein the first addend is encoded based on mappings of subvalues of the first addend to n sets of bases respectively associated with the n bases of the address representation, wherein the second subsequence of bases is a ternary encoding of the second addend over a set of three bases not including the particular base, and wherein the data representation is uncorrelated with each of the address representation and the further address representation; and storing, in a computer memory, the integer value.

2. The method of claim 1, wherein the reading involves using a primer with the address representation to locate the physical nucleotide sequence within a plurality of nucleotide sequences, wherein the primer consists of approximately 50% guanine and cytosine content and is self-uncorrelated, wherein address representations of the plurality of nucleotide sequences are mutually uncorrelated with one another.

3. The method of claim 1, wherein the ternary encoding of the second addend represents each of digits 0, 1, and 2, with respective different bases of the set of three bases.

4. The method of claim 1, wherein the physical nucleotide sequence does not contain folding structures.

5. The method of claim 1, wherein the n sets of bases exclude the particular base and the respectively associated bases of the address representation.

6. The method of claim 1, wherein the physical nucleotide sequence consists of approximately 50% guanine and cytosine content.

7. The method of claim 6, wherein the physical nucleotide sequence consisting of approximately 50% guanine and cytosine content comprises the physical nucleotide sequence being 0 to 3 bases away from 50% guanine and cytosine content.

8. The method of claim 1, wherein L is less than n, the first subsequence of bases is zero length, and the second subsequence of bases is L length.

9. The method of claim 1, wherein the n bases of the address representation are ordered such that no proper prefix of length j, for all j greater than or equal to a pre-defined integer k and less than n, is a suffix of the further address representation.

10. The method of claim 1, further comprising:
before reading the physical nucleotide sequence, selecting the address representation and the further address representation from a population of address representations so that the data representation is uncorrelated with the address representation and the further address representation; and
synthesizing the physical nucleotide sequence to be the address representation followed by the data representation, followed by the further address representation.

11. The method of claim 1, wherein the reading also involves locating an address sequence corresponding to the address representation in an unordered mixture of physical nucleotide sequences, and wherein the address sequence is associated with a data sequence corresponding to the data representation.

12. A system comprising:
means for reading, by way of random access, a physical nucleotide sequence of 2n+L bases to form a digital representation of the physical nucleotide sequence, wherein the reading involves amplifying the physical nucleotide sequence and sequencing the physical nucleotide sequence;
means for dividing the digital representation of the physical nucleotide sequence into an address representation of n bases, followed by a data representation of L bases, followed by a further address representation of n bases, wherein the address representation and the further address representation each are uncorrelated with one another, self-uncorrelated, and end with a particular base;
means for decoding the data representation into an integer value less than 3L that is a sum of a first addend and a second addend, wherein the data representation includes a first subsequence of bases encoding the first addend followed by a second subsequence of bases encoding the second addend, wherein the first addend is encoded based on mappings of subvalues of the first addend to n sets of bases respectively associated with the n bases of the address representation, wherein the second subsequence of bases is a ternary encoding of the second addend over a set of three bases not including the particular base, and wherein the data representation is uncorrelated with each of the address representation and the further address representation; and
means for storing, in a computer memory, the integer value.

13. The system of claim 12, wherein the reading involves using a primer with the address representation to locate the physical nucleotide sequence within a plurality of nucleotide sequences, wherein the primer consists of approximately 50% guanine and cytosine content and is self-uncorrelated, wherein address representations of the plurality of nucleotide sequences are mutually uncorrelated with one another.

14. The system of claim 12, wherein the ternary encoding of the second addend represents each of digits 0, 1, and 2, with respective different bases of the set of three bases.

15. The system of claim 12, wherein the physical nucleotide sequence does not contain folding structures.

16. The system of claim 12, wherein the n sets of bases exclude the particular base and the respectively associated bases of the address representation.

17. The system of claim 12, wherein the physical nucleotide sequence consists of approximately 50% guanine and cytosine content, and wherein the physical nucleotide sequence consisting of approximately 50% guanine and cytosine content comprises the physical nucleotide sequence being 0 to 3 bases away from 50% guanine and cytosine content.

18. The system of claim 12, wherein L is less than n, the first subsequence of bases is zero length, and the second subsequence of bases is L length.

19. The system of claim 12, wherein the n bases of the address representation are ordered such that no proper prefix of length j, for all j greater than or equal to a pre-defined integer k and less than n, is a suffix of the further address representation.

20. A method comprising:
selecting an address representation and a further address representation, each specifying nucleotide sequences of n bases, wherein the address representation and the further address representation are mutually uncorrelated;
selecting a data representation of a nucleotide sequence of L bases, wherein the data representation encodes an integer value less than 3L that is a sum of a first addend and a second addend, wherein the data representation includes a first subsequence of bases encoding the first addend followed by a second subsequence of bases encoding the second addend, and wherein the data representation is uncorrelated with the address representation and the further address representation;
concatenating the address representation with the data representation and the further address representation to form a representation of a physical nucleotide sequence of 2n+L bases; and
synthesizing the physical nucleotide sequence.

* * * * *